United States Patent
East et al.

(10) Patent No.: US 10,002,546 B2
(45) Date of Patent: Jun. 19, 2018

(54) SPINAL INJECTION TRAINER AND METHODS THEREFOR

(71) Applicant: BIOTRAS HOLDINGS, LLC, Addison, TX (US)

(72) Inventors: Johnny Wayne East, Fort Worth, TX (US); Brandon Knutson, Addison, TX (US); Edwin V. East, Jr., Addison, TX (US); Shane Funk, Addison, TX (US)

(73) Assignee: Biotras Holdings, LLC, Addison, TX (US)

( * ) Notice: Subject to any disclaimer, the term of this patent is extended or adjusted under 35 U.S.C. 154(b) by 0 days. days.

(21) Appl. No.: 15/608,652

(22) Filed: May 30, 2017

(65) Prior Publication Data
US 2017/0263158 A1     Sep. 14, 2017

Related U.S. Application Data

(63) Continuation-in-part of application No. 15/097,006, filed on Apr. 12, 2016, now Pat. No. 9,666,102, which is a continuation-in-part of application No. 14/818,137, filed on Aug. 4, 2015, now Pat. No. 9,378,661, which is a continuation-in-part of
(Continued)

(51) Int. Cl.
| | |
|---|---|
| *G09B 23/30* | (2006.01) |
| *G09B 23/28* | (2006.01) |
| *A61B 17/16* | (2006.01) |
| *G09B 23/34* | (2006.01) |
| *B29C 45/14* | (2006.01) |
| *A61B 5/00* | (2006.01) |

(52) U.S. Cl.
CPC ........ *G09B 23/285* (2013.01); *A61B 17/1671* (2013.01); *B29C 45/14795* (2013.01); *G09B 23/28* (2013.01); *G09B 23/30* (2013.01); *G09B 23/306* (2013.01); *G09B 23/34* (2013.01); *A61B 5/4566* (2013.01)

(58) Field of Classification Search
None
See application file for complete search history.

(56) References Cited

U.S. PATENT DOCUMENTS

| | | |
|---|---|---|
| 2,207,153 A | 7/1940 | Judovich |
| 2,689,415 A | 9/1954 | Haver |
| 6,780,016 B1 | 8/2004 | Toly |
| (Continued) | | |

OTHER PUBLICATIONS

NASCO (Fort Atkinson) Plastics; Lifeform: Spinal Injection Simulator LF01036U Instruction Manual; NP 161-83/RV 7-15; 6 pages; www.enasco.com.
(Continued)

*Primary Examiner* — James Hull
(74) *Attorney, Agent, or Firm* — Gregory M. Howison

(57) ABSTRACT

A model for anatomical training includes a clear thermoplastic elastomer matrix formed with at least one contoured surface that simulates at least a portion of a human body. The visibly clear thermoplastic elastomer matrix provides visible needle tracks upon needle penetration that may be fused closed upon heating the thermoplastic elastomer matrix. The model includes at least a portion of a vertebral column with a synthetic spinal sheath passing through a portion of the vertebral column, the synthetic spinal sheath providing tactile feedback upon needle penetration that simulates the tactile feedback of a needle penetrating a natural human spinal sheath.

18 Claims, 22 Drawing Sheets

Related U.S. Application Data application No. 14/325,391, filed on Jul. 8, 2014, now Pat. No. 9,280,915.

(60) Provisional application No. 61/847,564, filed on Jul. 18, 2013.

(56) References Cited

U.S. PATENT DOCUMENTS

| | | | |
|---|---|---|---|
| 7,866,984 B1 | 1/2011 | Jawalekar | |
| 8,403,675 B2 | 3/2013 | Stoianovici et al. | |
| 9,017,080 B1 | 4/2015 | Placik | |
| 2004/0236425 A1 | 11/2004 | Huang | |
| 2005/0035282 A1 | 2/2005 | Lehmann et al. | |
| 2005/0106545 A1 | 5/2005 | Heruth et al. | |
| 2006/0191544 A1 | 8/2006 | Simmonds et al. | |
| 2007/0290446 A1 | 12/2007 | Amick | |
| 2009/0142741 A1 | 6/2009 | Ault et al. | |
| 2010/0055657 A1 | 3/2010 | Goble et al. | |
| 2010/0167254 A1 | 7/2010 | Nguyen | |
| 2010/0269581 A1 | 10/2010 | Giurintano et al. | |
| 2010/0311025 A1 | 12/2010 | Everett | |
| 2012/0034587 A1 | 2/2012 | Toly | |
| 2013/0045469 A1 | 2/2013 | Noras | |
| 2014/0272873 A1 | 9/2014 | Svensson et al. | |
| 2014/0272881 A1 | 9/2014 | Barsoum | |

OTHER PUBLICATIONS

Jia Wei Li, Mphil, Manoj K. Karmakar, MD, Xiang Li, PhD, Wing Hong Kwok, Fanzca and Warwick Dean Ngan Kee, MD; Gelatin-Agar Lumbosacral Spine Phantom; Journal of Ultrasound in Medicine, Feb. 1, 2011, vol. 30, No. 2 263-272, www.jultrasoundmet.org.

Computer Imaging Reference Systems, Inc., "Lumbar Training Phantom Model 034", accessed at: http://www.cirsinc.com/products/all/8/lumbar-training-phantom/.

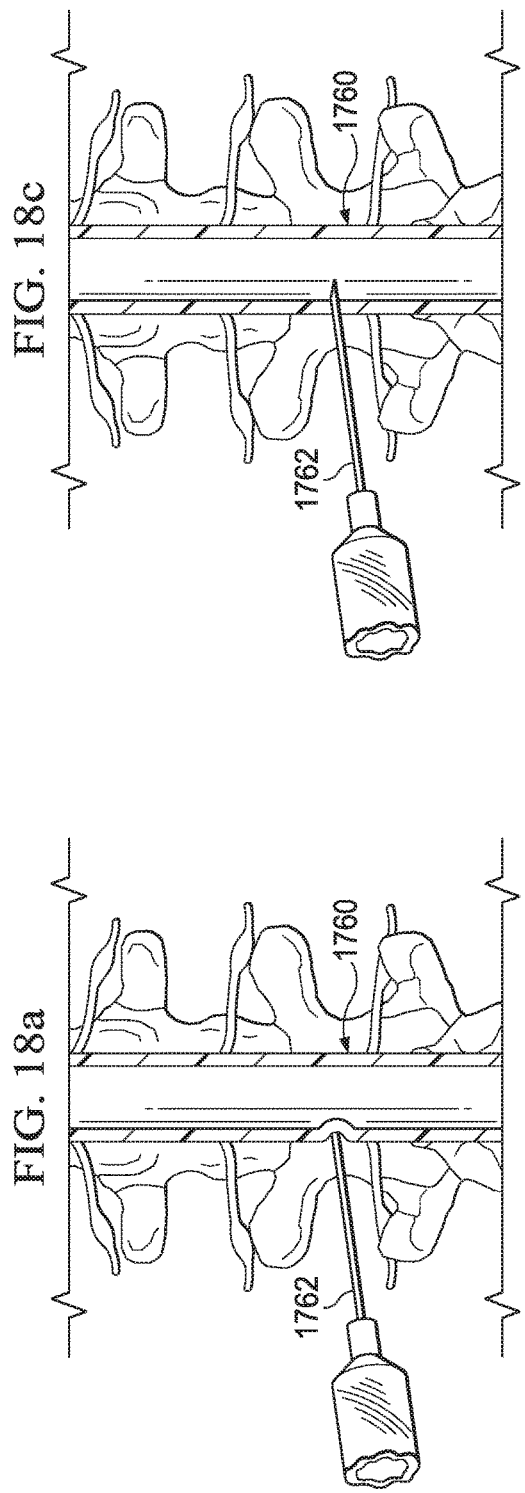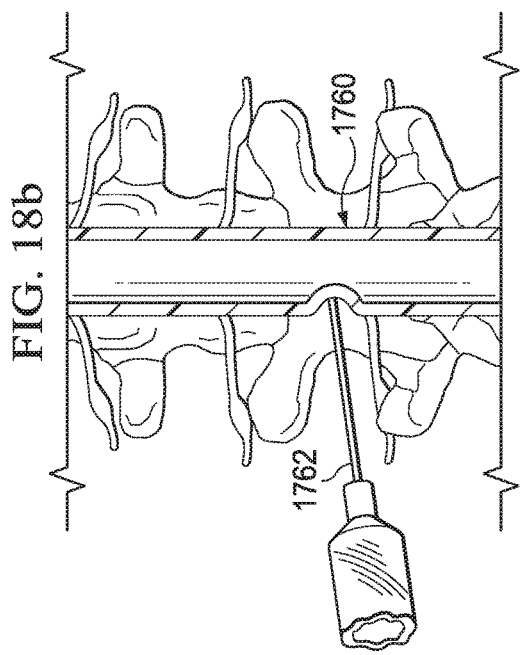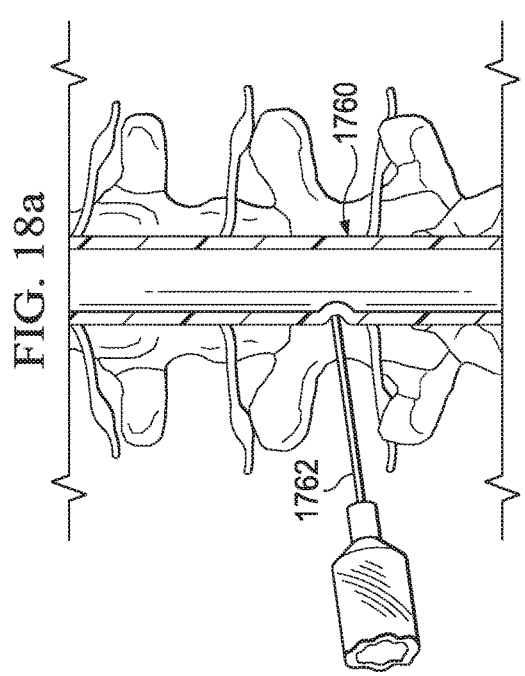

SPINAL INJECTION TRAINER AND METHODS THEREFOR

CROSS-REFERENCE TO RELATED APPLICATIONS

This application is a Continuation-In-Part of U.S. patent application Ser. No. 15/097,006, filed on Apr. 12, 2016, entitled SPINAL INJECTION TRAINER AND METHODS THEREFOR, now U.S. Pat. No. 9,666,102, issued May 30, 2017, which is a Continuation-In-Part of U.S. patent application Ser. No. 14/818,137, filed on Aug. 4, 2015, entitled SPINAL INJECTION TRAINER AND METHODS THEREFOR, now U.S. Pat. No. 9,378,661, issued Jun. 28, 2016, which is a Continuation-In-Part of U.S. patent application Ser. No. 14/325,391, filed on Jul. 8, 2014, entitled SPINAL INJECTION TRAINER AND METHODS THEREFOR, now U.S. Pat. No. 9,280,915, issued Mar. 8, 2016 which claims benefit of U.S. Provisional Application No. 61/847,564, filed on Jul. 18, 2013, entitled SPINAL INJECTION TRAINER AND METHODS THEREFOR. U.S. patent application Ser. Nos. 15/097,006, 14/818,137, 14/325,391 and 61/847,564 are incorporated herein by reference in their entirety.

TECHNICAL FIELD

The present invention relates generally to medical training models and more particularly to a model that includes natural vertebrae embedded in a matrix of clear synthetic ballistic gel, and its uses.

BACKGROUND

While use of cadavers has been declining in U.S. Medical schools primarily due to cost of preparing and maintaining the corpus, anatomists have complained that cadavers are still the best way to teach anatomy because it provides kinesthetic reinforcement as opposed to computerized models. Although anatomical teaching models are better now than in the past, a common material used to simulate tissue, silicone, although superior to other less resilient plastics, still does not provide the tactility of human tissue.

Spinal models for injection technique practice or training have been described in the past. Computerized Imaging Reference Systems, Inc, Norfolk Va., offers a lumbosacral spine model that includes a radiopaque plastic spinal model embedded in silicone. Other models including natural gelatin based embedded spinal phantoms for ultrasound use have been described; Jia Wei et al. "Gelatin-Agar Lumbosacral Spine Phantom" J Ultrasound Med (2011) 30:263-272, describes an agar-gelatin matrix and Bellingham et al., "A Low-Cost Ultrasound Phantom of the Lumbosacral Spine" Regional Anesthesia and Pain Medicine (2010) vol. 35, no. 3, describes a concentrated gelatin matrix. However, neither silicone models nor the described natural gelatin based matrices provide realistic tactile feedback for the trainee.

Natural gelatin is a material obtained from collagen and other animal by-products and is a component in numerous foods and cosmetic products. More particularly, "ballistic" gel is a formulation based on either natural gelatin or a synthetic, which is calibrated to possess ideally, characteristics similar to human muscle tissue, and is used primarily in ballistics testing. One standard calibration of ballistic gel involves firing into it a 0.177 caliber steel BB, from an air gun, measuring the velocity of the projectile and the depth of penetration. Ballistic gels based on natural gelatin will darken, degrade quickly, and cannot be reused. Because bacterial contamination and decay are a concern, natural gelatin based models must be refrigerated between uses. While training phantoms employing skeletal replicas are adequate for sonographically guided needle insertion, plain plastic or resin components will not show adequately in either plain x-ray or fluoroscopic imaging because they are non-radiopaque. In the case of x-rays, bone appears lighter than the surrounding tissue. In a fluoroscope, relatively more x-rays pass through soft tissue to fluoresce on a phosphor screen and produce real time moving images wherein the bones appear relatively darker than the surrounding tissue. While some practice models employ plastic vertebrae made of radiopaque resin enabling it to be seen in a fluoroscope monitor, the image contrast provided by radiopaque plastic is unlike that of natural bone because of the naturally non-uniform distribution of calcium in bone which selectively absorbs more or less of the x-rays, thereby producing a more dimensional image.

Both silicone "tissue" of costly training models and the relatively inexpensive gelatin based phantoms break down with repeated punctures rendering them unfit for training. At some point, accumulated needle tracks will interfere with both light transmission, clarity and disturb the intended path and placement of subsequent needles. It would be desirable to provide a teaching model for the human spine that provides realistic tactile feedback of the vertebral column and surrounding tissue. It would be further desirable if such models were suitable for fluoroscopically guided spinal injection techniques. In addition to being reusable and requiring no refrigeration, the foregoing model should produce an image that reflects actual natural bone contour, and be transparent so that needle path and placement can be observed or practiced with or without the use of imaging techniques such as fluoroscopy or sonography.

SUMMARY

The present invention seeks to address the shortcomings of past spinal training models by providing a spinal model that includes a complete vertebral column that is embedded in a matrix of crystal clear ballistic gel. The synthetic gel does not harbor bacteria, can be reused and does not require refrigeration. Natural bone typically provides better image contrast than synthetic radiopaque replicas. More dimensional, i.e., contoured image contrast, is obtainable with natural bone which is obtained via cadavers or antique teaching skeletons. For use in training needle techniques such as spinal anesthesia and or lumbar epidural steroid injections, a transparent synthetic gel matrix permits observation of needle progression by both the trainee and the trainer and provides unique opportunities for coaching and intercession to prevent poor needle placement prior to its occurrence. Because the matrix closely simulates the feel of human tissue, for purposes of anatomy instruction, a flexible opaque sheet of a self-healing material such as closed cell polyurethane foam or similar material, having a thickness between 2 and 10 mm, may be placed over the model so that the structures and regions of the spine can be taught, and later independently discerned, without benefit of visual reinforcement.

In one embodiment, a model for anatomic training and injection practice includes a visibly clear thermoplastic elastomer matrix formed with at least one anatomically contoured surface. The anatomically contoured surface simulates at least a portion of a human body while the visibly clear thermoplastic elastomer matrix provides visible needle tracks upon needle penetration. The visible needle tracks are fused closed upon heating the thermoplastic elastomer matrix such that the needle tracks are no longer visible in the thermoplastic elastomer matrix. A skeletal structure is embedded within the synthetic gel matrix at the same location, relative to the anatomically contoured surface, as the corresponding skeletal structure is located in a human body. The skeletal structure is selected to produce a fluoroscopic image representative of human bone corresponding to the skeletal structure. The visibly clear thermoplastic elastomer matrix provides tactile feedback substantially similar to human tissue. The model may include a form for receiving the visibly clear thermoplastic elastomer matrix and skeletal structure, the form having anatomically contoured portions simulating surfaces of at least a portion of a human body. In one embodiment, at least a portion of the skeletal structure is natural human bone.

In one aspect, a selected portion or portions of the visibly clear thermoplastic elastomer matrix may be replaced by removing the selected portion, replacing the removed selected portion with a new replacement portion and applying heat to fuse the replacement portion into the model. The model may also include at least one heat source embedded in the visibly clear, thermoplastic elastomer matrix to provide localized heating of a portion of the visibly clear thermoplastic elastomer matrix to fuse needle tracks formed in the matrix. The heat source may be positioned adjacent to one or more portions of the vertebral column, for example, adjacent the vertebral column.

The model may also include one or more embedded light sources, for example a plurality of LEDs, whereby the light source increases the visibility of needle tracks formed in the in the visibly clear thermoplastic elastomer matrix. The light source may be embedded in the visibly clear thermoplastic elastomer matrix adjacent at least a portion of the skeletal structure, for example, the vertebral column, to enhance viewing of needle tracks resulting from needle penetration in the region of the matrix surrounding the skeletal structure.

In another aspect, the embedded skeletal structure may be a partial or complete vertebral column. The model may also include synthetic simulated soft tissue structure such as one or more synthetic intervertebral discs, a simulated spinal cord and simulated spinal nerves. The model may also include surgical hardware installed, for example, on the embedded vertebral column and a heat source embedded in the synthetic gel matrix adjacent at least a portion of the vertebral column to provide localized heating of a portion of the visibly clear thermoplastic elastomer matrix to fuse needle tracks formed in the matrix and/or fuse a replacement portion of the matrix. Radiopaque markers may be embedded in the visibly clear thermoplastic elastomer matrix adjacent selected portions of the skeletal structure. The radiopaque markers may serve as targets for needle insertion practice.

In one variation, the visibly clear thermoplastic matrix comprises from about 15% wt % to about 20 wt % of a rubbery block copolymer and from about 80% to about 85% of a white oil. The rubbery block copolymer may comprise an SEBS (styrene-ethylene/butylene-styrene) block copolymer. In one embodiment, the rubbery block copolymer has a tensile stress of from about 8.00 to about 10 psi, a tensile strength at break of from about 140 to about 170 psi and a tensile elongation at break of from about 500 to about 1500%.

In another aspect, a method of preparing a model for anatomic training, includes the step of saturating an open cell foam with a liquid thermoplastic elastomer to form an impregnated elastomer impregnated foam. The thermoplastic elastomer is cured and a simulated intervertebral disc is formed from the elastomer impregnated foam. A first, thin layer of liquid silicone is applied to the simulated intervertebral disc which is positioned between vertebrae to form a skeletal structure. The skeletal structure is placed in a mold having at least one surface anatomically contoured surface simulating at least a portion of a human body. Liquid, visibly clear, thermoplastic elastomer is then added to the mold. The visibly clear thermoplastic elastomer matrix provides visible needle tracks upon needle penetration for training purposes. The visible needle tracks may be fused closed by heating the thermoplastic elastomer matrix so that the needle tracks are no longer visible in the thermoplastic elastomer matrix. The skeletal structure is embedded within the visibly clear thermoplastic elastomer at the same location, relative to the anatomically contoured surface, as the corresponding skeletal structure is located in a human body and produces a fluoroscopic image representative of actual bone corresponding to the skeletal structure.

In an alternate embodiment, a model for anatomic training and injection practice includes a visibly clear thermally fusible synthetic gel matrix formed with at least one contoured surface that simulates a partial human torso. A skeletal structure including at least a portion of a vertebral column with vertebra is embedded within the synthetic gel matrix at the same location as the corresponding skeletal structure is located in a human. At least a portion of the skeletal structure produces a fluoroscopic mage with an image contrast representative of human bone. A synthetic spinal sheath passes through at least a portion of the vertebral column, providing tactile feedback upon needle penetration that simulates the tactile feedback of a needle penetrating a natural human spinal sheath. The synthetic gel matrix retains visible tracks resulting from needle penetration and extraction of a needle alone the path of the needle after insertion at a point on the contoured surface to a target below the contoured surface, at least a portion of the needle tracks extending alone the path remaining visible until the needle tracks are fused closed with a heat source such that the needle tracks are no longer visible in the synthetic gel matrix. In one aspect, the synthetic spinal sheath is formed from flexible elastic latex, tubing having an inside diameter of ⅜ inch, an outside diameter of ⅝ inch and a wall thickness of ⅜ inch. The synthetic spinal sheath is selected to have a resistance to needle penetration sufficient to simulate needle penetration of a human myelin spinal sheath.

In one variation, a method of making a model for anatomic training and injection practice includes the steps of (a) assembling a skeletal structure with at least a portion of a vertebral column including a synthetic spinal sheath passing through the at least a portion of the vertebral column, the synthetic spinal sheath providing tactile feedback upon needle penetration that simulates the tactile feedback of a needle penetrating a natural human spinal sheath with the portion of the vertebral column producing a fluoroscopic image representative of the structure of human bone, (b) positioning the skeletal structure in a mold having a contoured portion simulating a partial torso, and (c) embedding the skeletal structure in a visibly clear, thermally fusible, synthetic ballistic gel matrix, wherein, upon curing, the skeletal structure is positioned, relative to the contoured surface, at the same location as the corresponding skeletal structure is located in a human torso, and wherein at least a portion of visible needle tracks formed through the synthetic gel matrix along the path of a needle upon insertion at a point on the contoured surface to a target below the contoured surface remain visible until the needle tracks are fused closed. In one aspect, a flexible bladder may be placed within the skeletal structure at a location corresponding to the thoracic and/or abdominal cavity and inflated before embedding the skeletal structure in the visibly clear, thermally fusible, synthetic ballistic gel matrix to reduce the volume of gel used to form the model. The bladder may be removed after the gel solidifies, leaving a void or cavity in the model that significantly reduces the weight of the model.

BRIEF DESCRIPTION OF THE DRAWINGS

FIG. 18a-18c are partial views of the model of FIG. 17 illustrating needle penetration of the synthetic spinal sheath;

DETAILED DESCRIPTION

Figure 1:
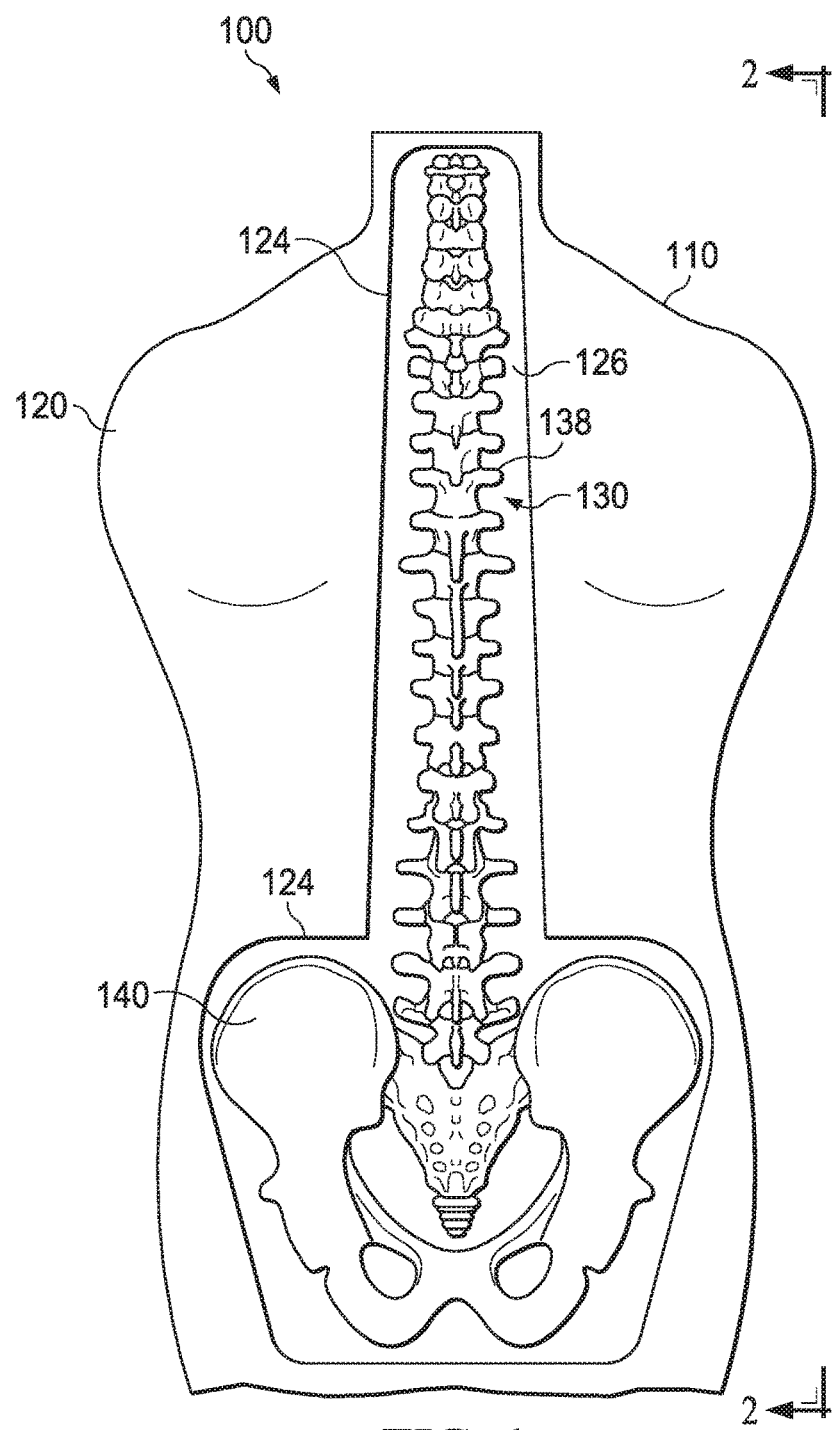
FIG. 1 is a top view of a first embodiment a spinal injection trainer a according to the disclosure.
Figure 2:
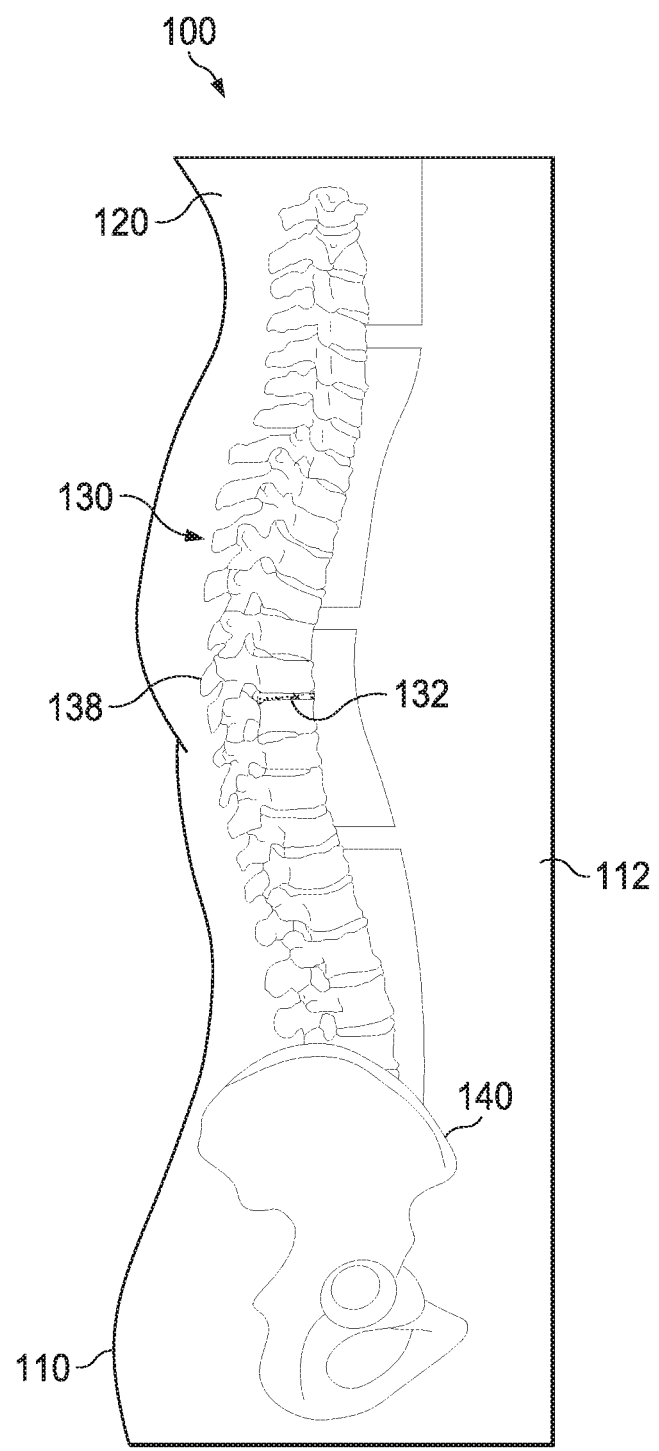
FIG. 2 is a lengthwise cross-sectional view taken along lines 2-2 of the embodiment shown in FIG. 1.

FIGS. 1 and 2 are partial top and side views of a spinal injection training model 100. As illustrated, model 100 includes a complete vertebral column 130 and pelvic bone 140 embedded in synthetic gel matrix 120 along with simulated intervertebral discs 132. In one embodiment, matrix 120 is a transparent synthetic ballistic gel having a density and feel substantially similar that of human tissue in order to provide realistic haptic feedback upon needle insertion and placement. The transparent synthetic ballistic gel also provides realistic haptic feedback during spinal palpation practice. The synthetic gel does not harbor bacteria, can be reused and does not require refrigeration. Synthetic ballistic gels have been formulated to have some of the properties of natural gelatin, but are odorless and colorless, and unlike natural gelatin, can be reused by heating and reforming by melting and re-pouring into a form. Two U.S. companies that make or sell synthetic ballistic gel are Clear Ballistics LLC., P.O. Box 723, Fort Smith, Ark. 72901, and Ballistek Gel LLC, N8547 North Rd, Ixonia, Wis. 53036. In different embodiments, other materials simulating the feel of human tissue may be used.

One material suitable for use as synthetic gel matrix 120 is a visibly clear thermoplastic elastomer comprising approximately 15 wt % of a rubbery block copolymer with approximately 85 wt % of white oil. In one embodiment, 16.6 wt % SEBS (styrene-ethylene/butylene-styrene) block copolymer is mixed with 83.4 wt % of a white oil and the mixture is heated to approximately 250° F. and allowed to cool. Upon cooling, the mixture forms a clear, thermoplastic elastomer suitable for use as synthetic gel matrix 120. A suitable material for use as synthetic gel matrix 120 has a specific gravity of 0.87 (ASTM D792), a tensile stress of 9.00 psi (ASTM D412), a tensile strength at break of 154 psi (ASTM D412), a tensile elongation at break of 1300% (ASTM D412), a tear strength of 40 lbf/in (ASTM D624), a durometer hardness of 30 (Shore 00, 10 sec, ASTM D2240) and an apparent viscosity of 1.30 Pas (392° F., 11200 sec-1 ASTM D3835). The material is water clear and has a texture and feel that simulates human tissue.

In different embodiments, synthetic gel matrix 120 may comprise a thermoplastic elastomer comprising from about 15 to about 20 wt % of an elastomeric block copolymer such as an SEBS (styrene-ethylene/butylene-styrene) block copolymer mixed with from about 80 to about 85 wt % of a white oil. Suitable materials for use as synthetic gel matrix 120 may have a specific gravity of from about 0.80 to about 0.90 (ASTM D792), a tensile stress of from about 8.00 to about 10 psi (ASTM D412), a tensile strength at break of from about 140 to about 170 psi (ASTM D412), a tensile elongation at break of from about 500 to about 1500% (ASTM D412), a tear strength of from about 30 to about 50 lbf/in (ASTM D624), a durometer hardness of from about 25 to about 35 (Shore 00, 10 sec, ASTM D2240) and an apparent viscosity of from about 1.20 to about 1.40 Pas (392° F., 11200 sec^-1 ASTM D3835). Such materials will have a density and elastic properties that provide a feel, texture and resistance to needle insertion similar to human tissue.

A form or mold 110 containing matrix 120 includes an upper opening 124 that exposes a portion of the upper surface 126 of synthetic gel matrix 120 for needle insertion practice. Mold 110 may be formed from a rigid material such as an acrylic, a polycarbonate or a metal. In some applications, model 100 may be transported or stored in mold 110 to protect the model. In different embodiments, mold 110 may be partially contoured to simulate the surfaces of a partial or complete human torso, a torso with a head and neck, or any desired portion of a human body, depending upon the particular application. In the embodiment illustrated in FIGS. 1 and 2, mold 110 is anatomically contoured on one side to simulate the surface of the back of a human torso while in other embodiments mold 110 may be anatomically contoured to simulate a complete human torso.

In one embodiment, vertebral column 130 is natural bone, in other embodiments vertebral column 130 may be formed from materials that provide contrast during fluoroscopic imaging that simulates or is representative of human bone. In an embodiment where vertebral column 130 is human bone, the vertebral column may be obtained from cadaverous specimens, or from antique skeletal models. In other embodiments different sources of natural bone, such as animal bone, may be used to form vertebrae or simulations of vertebrae. To prepare the model, vertebrae 138 are first cleaned and treated with a sealant that is non-reactive with the thermoplastic elastomer matrix 120 and placed in anatomically contoured form 110 (mold) with the spinous processes pointing down, with the vertebral body facing up. Vertebral column 130 and pelvic bone 140 may be secured from shifting during the molding process with a jig or similar support structure or by other suitable means. In one embodiment, an insert 112 may be utilized to secure vertebral column 130 and pelvic bone in position during the molding process. Vertebral column 130 is embedded within synthetic gel matrix 120 at the same location, relative to the contoured surfaces of model 100, as the corresponding skeletal structure is located in a human torso. Since the bottom inside surface of mold 110 is contoured to resemble the curves of the human back, a uniform distance of about 2 cm will exist between the tops of spinous processes and the mold bottom.

One or more blocks of synthetic ballistic gel are placed into the mold void containing vertebral column 130 which is then heated in an oven to melt the gel. Once liquefied, the matrix may be subjected to vibration to raise trapped air to the surface. After the gel cools and firms, the top or upper surface of model 100 can be trimmed with a knife or wire to remove any bubbles. It is possible, of course to apply a vacuum for degassing the matrix to draw out trapped or entrained air, preferably prior to curing. In other variations, the synthetic gel may be melted in a separate container and then poured into mold 110 and allowed to solidify. After the synthetic gel has solidified, mold 110 may be removed from model 100. In some embodiments it may be desirable to leave model 100 in mold 110 for transportation or storage and/or provide one or more openings, such as opening 124, for access to the model.

Figure 3:
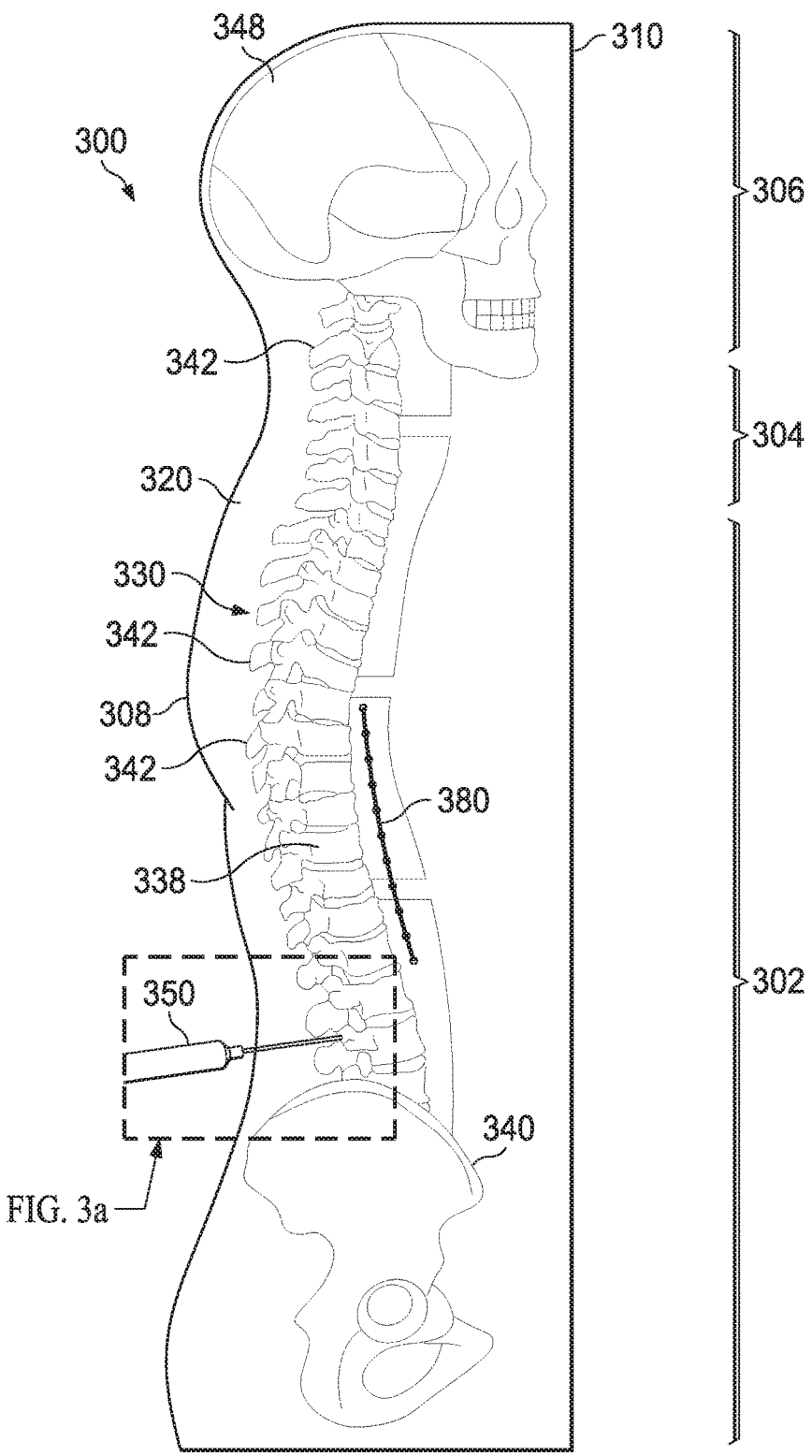
FIG. 3 is a side view of a second embodiment of a spinal injection trainer illustrating a needle insertion.

FIG. 3 is a side view of a second embodiment of a model 300 including a torso section 302, a neck section 304 and head section 306. A complete vertebral column 330, skull 348 and pelvic bone 340 are imbedded in synthetic gel matrix 320. In one embodiment, synthetic gel matrix 320 is formed from the thermoplastic elastomer described above in connection with matrix 120. Forming model 300 with neck section 304 and head section 306 provides a more realistic model for training purposes and is also useful in connection with chiropractic training and practice. In an embodiment where one or more complete vertebral column 330, skull 348 and pelvic bone 340 are natural bone, the contrast produced during a fluoroscopically-guided procedure will realistically simulate that of an actual in vivo procedure. In other embodiments a suitable synthetic material that provides contrast representative of natural bone may be employed to form skeletal structures. As illustrated the back or dorsal side 308 of model 300 is anatomically contoured to correspond to the typical contours of a human back, neck and head with the contour of the torso portion following the spinous processes 342 of vertebrae 338.

Model 300 may be molded and formed in the same or in a similar manner as described in connection with model 100. As illustrated, the front surface 310 of model 300 is essentially flat which provides a stable surface upon which the model may be placed, with a back (dorsal) surface anatomically contoured to match a human torso. Alternatively, model 300 could be molded with contours corresponding to the front, back and sides of the torso, neck and head of a typical human body. Model 300 could also be molded to correspond to a lesser or greater portion of a typical human body depending upon the particular use and application. Vertebral column 330, skull 348 and pelvic bone 340 are positioned in synthetic gel matrix 320, relative to the anatomically contoured surfaces of model 300, as the corresponding skeletal structure is positioned within a human body. Model 300 may be supplied in various sizes corresponding to different body types including obese body types, in which case synthetic gel matrix 320 would have a relatively greater thickness over spinous processes 342. This is particularly useful in chiropractic training as palpation of the spinal elements is key.

Figure 3A:
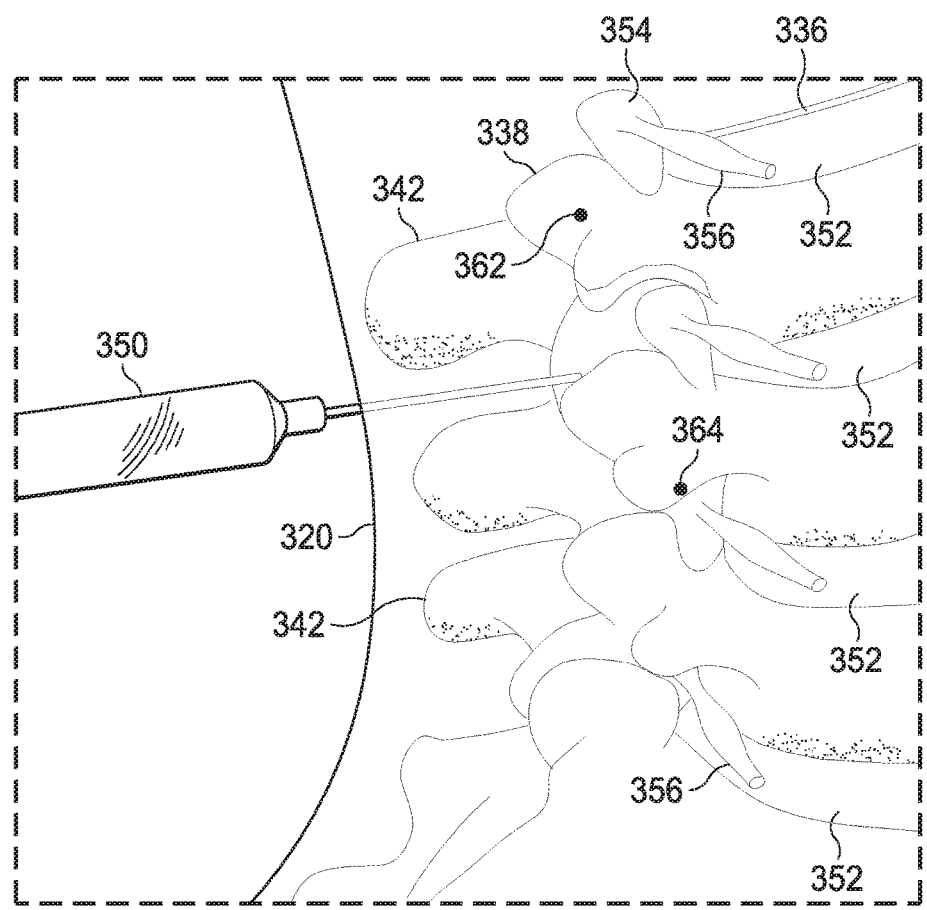
FIG. 3A is a detail view of a segment of spinal column of FIG. 3 illustrating foam discs positioned between vertebrae.

FIG. 3A is a detail view of the insertion of a needle 350 between vertebrae 338 such that the injection technique can be observed from any direction. As illustrated, a section of vertebral column 330 is provided with artificial foam discs 352 to simulate actual vertebral discs. Artificial foam discs 352 may be formed from urethane foam, silicone, or other suitable material that simulates the density of a human vertebral disc. Artificial foam discs 352 provide haptic feedback during needle insertion training as the force required to continue insertion of the needle from synthetic gel matrix into one of the artificial foam discs 352 will change when the needle penetrates the artificial foam disc. In one embodiment, foam discs 352 are formed with a silicone layer 336 on the upper and lower surfaces of the disc. Alternatively, foam discs 352 may be embedded in, or covered with, a silicone or urethane of a different density. In one embodiment, a simulated spinal cord 354 and a simulated spinal nerve 356 are embedded in synthetic gel matrix 320. Simulated spinal cord 354 and simulated spinal nerve 356 may be formed from a silicon or similar material to simulate actual tissue.

In some applications it may be desirable to provide a market or "target" for spinal injection training purposes. FIG. 3A illustrates the placement of radiopaque markers 362, 364 that may be used as targets for needle injection practice. Marker 362 corresponds to a target for a lumbar medial block injection and marker 364 serves a target for a lumbar transforaminal injection. Markers 362, 364 may be used as a guide during a fluoroscopically-scanned practice injection. Alternatively, a needle may be inserted into model 300 and, after insertion, a fluoroscopic scan may be used to determine how close to the target the tip of the needle was placed.

Figure 3B:
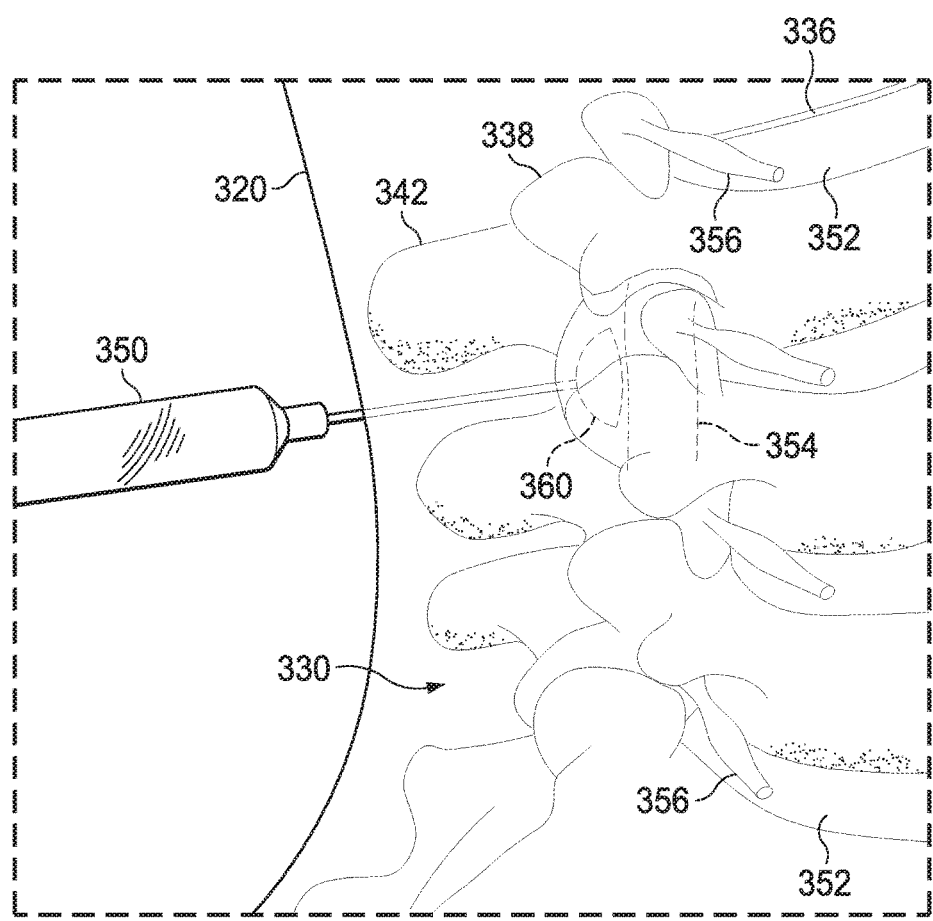
FIG. 3B is a detail view of a segment of spinal column of FIG. 3 illustrating the formation of a simulated epidural space.

Referring now to FIG. 3B, in one embodiment, a simulated epidural space 360 or void may be created in model 300. To form epidural space 360, needle 350 is connected to a source of compressed air (not shown) or suitable gas such as nitrogen and inserted to the desired location in vertebral column 330. Air is metered through needle 350 to create a bubble in synthetic gel matrix 320 at the desired location. In one variation, needle 350 is inserted through synthetic gel matrix 320 after model 300 has been molded, but before the synthetic gel has solidified, e.g., as the gel cools after molding. Simulated epidural space 360 provides haptic feedback during needle insertion training as the force required to continue insertion of the needle from the synthetic gel matrix 320 into the simulated epidural space will change when the needle penetrates the simulated epidural space.

Referring again to FIG. 3, in one embodiment, a light source 380 is embedded in synthetic gel matrix 320 of model 300. Light source 380 may be a plurality of LEDs, for example a linear strip of LEDs or a similar light source connected to an external power source (not shown). As illustrated, light source 380 is positioned adjacent a portion of vertebral column 330 on the anterior side of the column. In different embodiments light source 380 may be positioned on the dorsal side of vertebral column 330 or laterally on one or both sides of the column. Light source(s) 380 may be positioned adjacent only a selected portion of vertebral column 330, at several locations along column 380, or a plurality of light sources may be used to illuminate the entire model, including skull 348, vertebral column 330 and pelvic bone 340. Light from light source 380 is diffused by synthetic gel matrix 320 and serves to illuminate a needle during insertion practice and to illuminate needle tracks formed during needle insertion.

Figure 4:
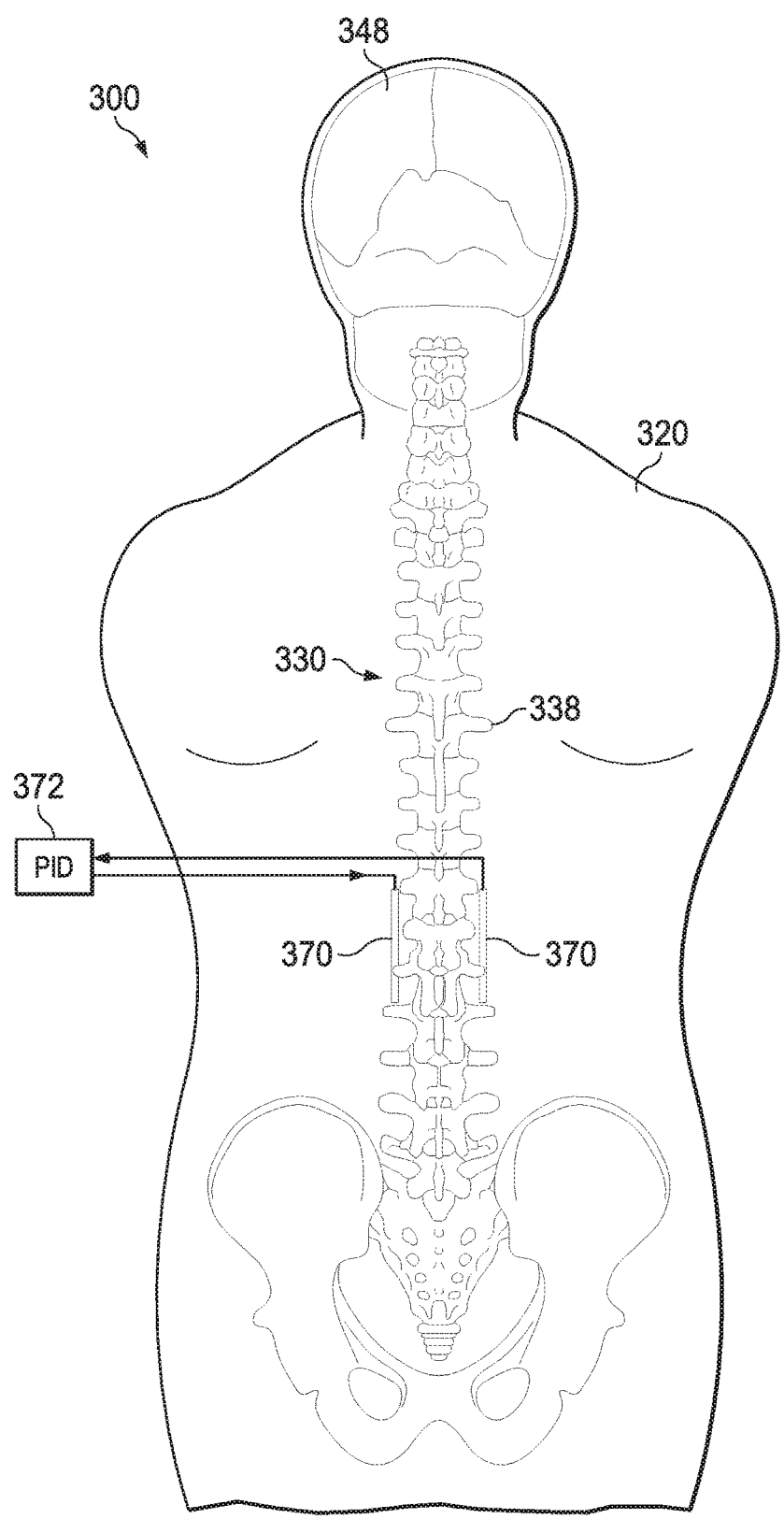
FIG. 4 is a top view illustrating one placement of heat sources in the spinal injection trainer of FIG. 3 heaters adjacent a portion of the spinal column.

FIG. 4 is top view of spinal model 300 wherein heaters 370 have been placed adjacent the spinal region where needle practice occurs. Heaters 370 are utilized to heat localized areas of synthetic gel matrix 320 to a temperature approaching the melting point of the matrix material. As the matrix material approaches the melting point, the synthetic gel matrix 320 softens and needle tracks in the heated area fuse and close, eliminating the needle tracks. In one variation, heaters 370 are cartridge heaters which may be placed on either side vertebral column 330 in an area utilized for needle practice. The cartridge heaters are preferably controlled by a PID controller 372 that can maintain a programmed temperature to within −0.5 to +0.5 degrees Celsius. PID control permits more stable temperature range management than other types of temperature control such as on/off control, or proportional control.

Suitable PID controllers for the invention include, but are not limited to auto-tune type controllers such as the EZ-ZONE PM Temperature Controller Series from Watlow Inc., 12001 Lackland Rd., St. Louis, Mo., USA, 63146, that provide for adaptive temperature sensing and learning, whereby the controller initially probes a material to determine its thermal properties which are then employed in the controller's PID algorithm. When it is desired that the needle tracks be erased, the controller can be set to cycle to a desired temperature that is where the synthetic gel matrix starts to transition to a flowable or liquid state, whereby the tracks are fused closed, after which the cartridge heaters cycle off. Cartridge heaters 370 are controlled such that the heaters do not exceed the melting point of the synthetic gel matrix material.

Figure 5:
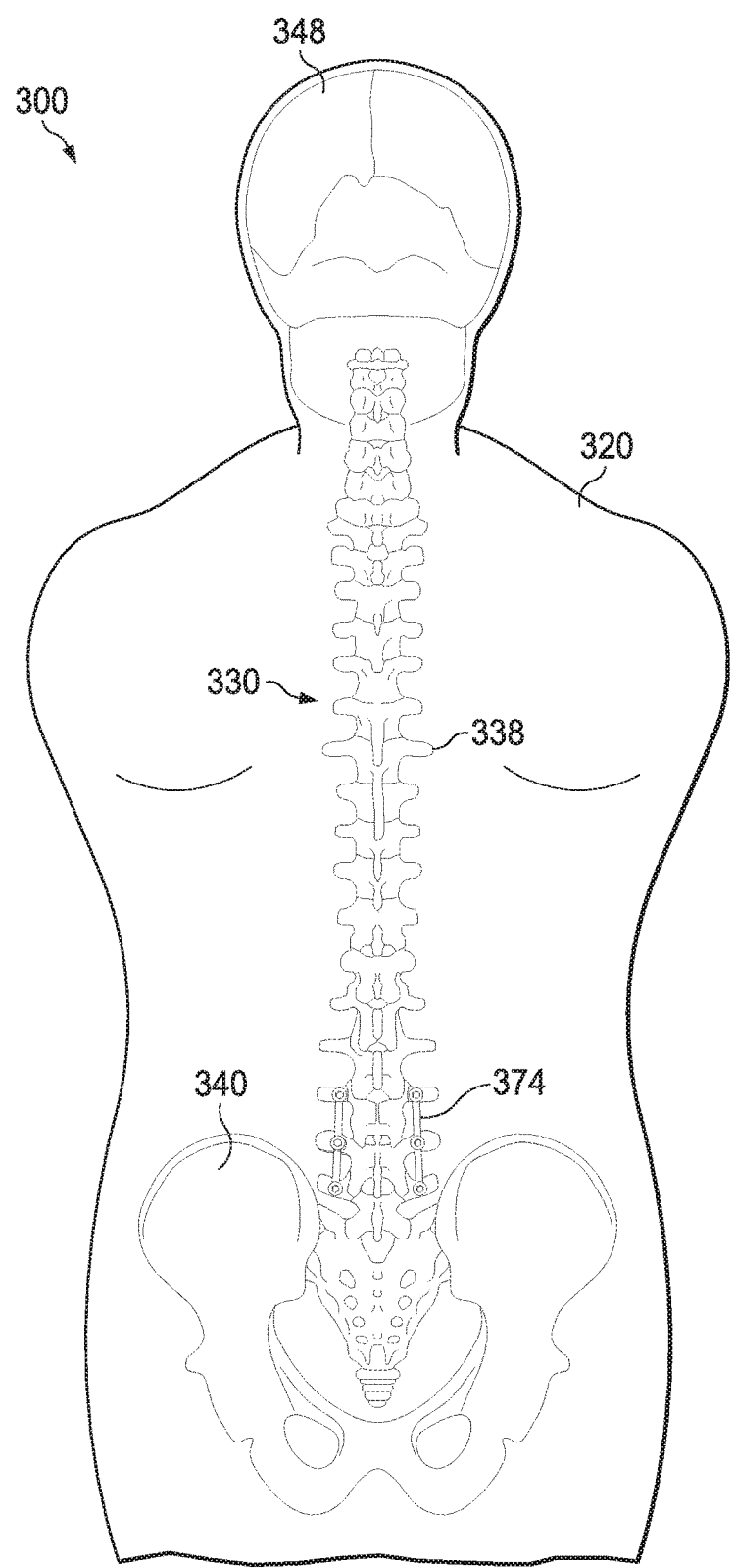
FIG. 5 is a top view illustrating one placement of surgical hardware on the spinal column.

FIG. 5 is top view of spinal model 300 including surgical hardware 374 installed on the embedded vertebral column 330. Spinal fusion surgery is a procedure wherein some or all of one or more vertebral discs are removed and replace with bone grafts. Metallic rods, brackets, clamps and threaded fasteners, such as surgical hardware 374 are used to keep the vertebra and grafts in place while the graft and bones grow together or fuse. However, surgical hardware 374 can mask or distort adjacent regions during imaging such that distinguishing spinal structures may be difficult. In order to provide an accurate postoperative assessment of spinal surgical hardware, practitioners should be familiar with the normal imaging appearances of the lumbar spine after procedures such as stabilization, fusion, and disc replacement. Spinal model 300 with surgical hardware 374 provides a means to familiarize practitioners with the visual and imaged normal appearance of vertebral column 330 spine after implantation of the surgical hardware. Spinal model 300 with surgical hardware 374 also provides a means of needle insertion practice training for cases where surgical hardware has been installed.

Figure 6:
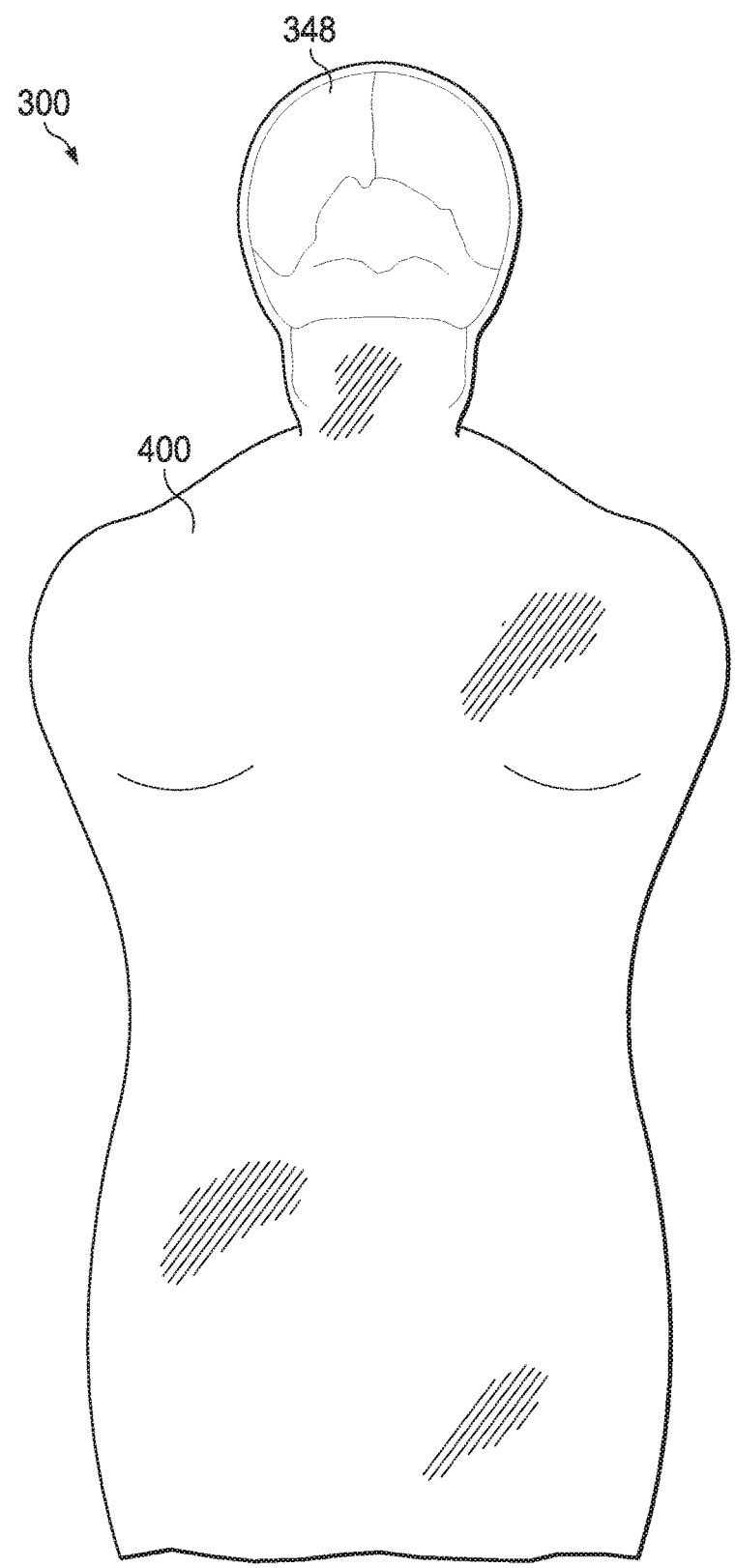
FIG. 6 shows the embodiment of FIG. 1 with a sheet placed over the contoured form.

FIG. 6 is a top view of model 300 partially covered with a flexible opaque sheet 400. Sheet 400 may be sized and shaped to fit the model and formed from a silicone or similar elastomer having a texture similar to human skin with a thickness of from about 2 mm to about 10 mm. In one embodiment, sheet 400 may be removable and fitted over model 300 when desired. In different embodiments, sheet 400 may be affixed to model 300 with an adhesive or otherwise attached to the model or molded onto the model by placing the sheet in mold 110 prior to placing the synthetic gel matrix material into the mold.

Sheet 400 allows for "blind" palpation and discernment of the spinous process 342 (FIG. 3) to simulate a clinical setting. Flexible opaque sheet 400 may be used during needle insertion practice with or without fluoroscopy. While the use of opaque sheet 400 prevents visual observation of needle 350 (FIG. 3) during insertion, use of the sheet during needle insertion provides a more realistic simulation of actual practice on a live patient. Likewise, while the use of opaque sheet 400 during spinal palpation practice prevents visual observation of vertebral column 130 during the practice, the use of the sheet provides a more realistic simulation of an actual procedure.

Figure 7:
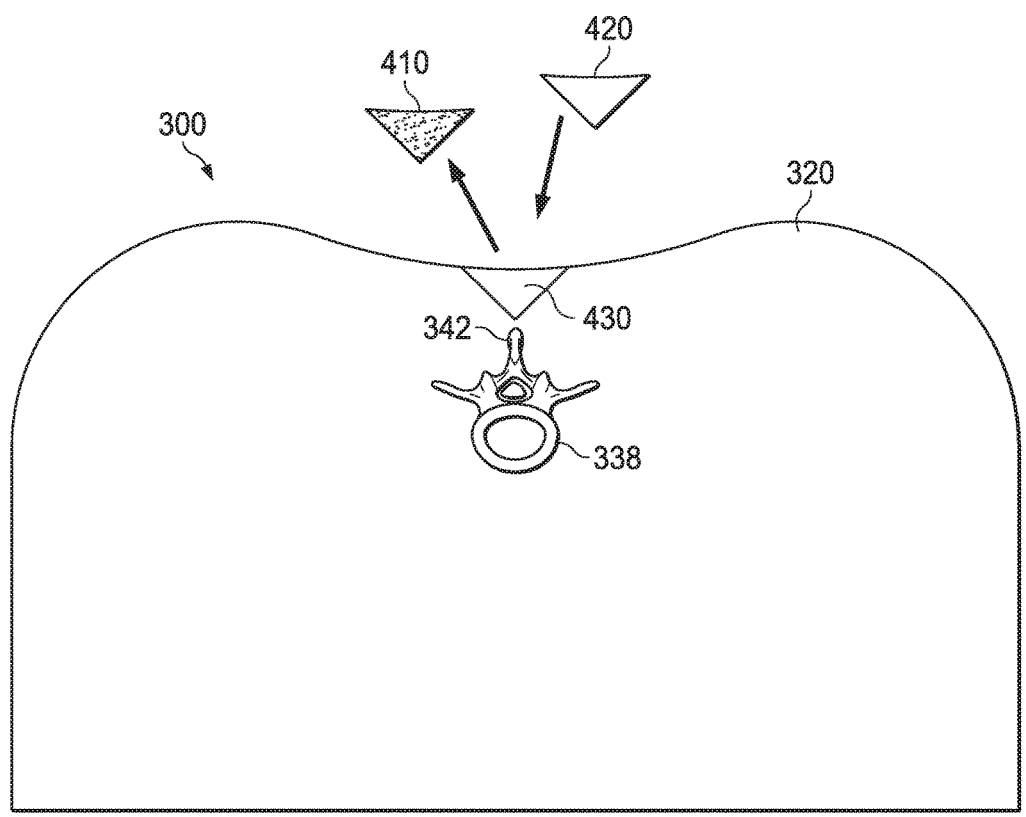
FIG. 7 is a cross-sectional view taken along lines 7-7 of the embodiment shown in FIG. 1 illustrating replacement of a portion of the model.

In some instances it may be desirable to replace a portion of synthetic gel matrix 320 without replacing the entire matrix, for example, if a portion of synthetic gel matrix 320 becomes discolored due to contamination or due to repeated reheating with heaters 370 (FIG. 4). FIG. 7 is a partial cross sectional view of model 300 illustrating a partial replacement of synthetic gel matrix 320. As illustrated, a discolored section 410 of synthetic gel matrix 320 is separated by cutting and removing the section from model 300. A replacement section 420 of synthetic gel is cut to fit the cavity or opening 430 created by the removal of section 410. The replacement section 420 is fitted into cavity 430 and heated to fuse the section into model 300. A localized area of model 300 may be heated to fuse replacement section 420 into model 300 with, for example, heaters 370 or another heat source. Alternatively, the entire model 300 may be placed into an over or similar enclosure and the model heated to fuse replacement section 420 in place. In either case, the replacement section and the adjacent portion of model 300 are heated to a temperature approaching, but not exceeding, the melting point of the synthetic gel matrix 320 to fuse the replacement section 420 to model 300.

Although the models described and illustrated herein include a human vertebral column, models of different portions of human anatomy with different skeletal structures may be constructed. For example, a model of a human leg, arm foot or other body portion may be formed from a thermoplastic elastomer matrix as described above with embedded natural or synthetic bones and/or synthetic soft tissue structures to provide a practice model for injections and arthroscopic surgery. Such models may also be provided with embedded light sources, radiopaque markers or targets and/or surgical hardware. Models may also be constructed for veterinary applications.

Accordingly, a model for anatomic training includes a visibly clear thermoplastic elastomer matrix having at least one anatomically contoured surface that simulates at least a portion of a human body and provides tactile feedback similar to human tissue. The visibly clear thermoplastic elastomer matrix provides visible needle tracks upon needle penetration that are fused closed upon heating the thermoplastic elastomer matrix such that the needle tracks are no longer visible in the thermoplastic elastomer matrix. Selected portions of the model may be replaced by removing the selected portion of the visibly clear thermoplastic elastomer matrix, replacing the removed selected portion of the visibly clear thermoplastic elastomer matrix with a new replacement portion and applying heat to fuse the replacement portion into the model. A skeletal structure is embedded within the visibly clear thermoplastic elastomer matrix at the same location, relative to the anatomically contoured surface, as the corresponding skeletal structure is located in a human body. The skeletal structure may be a vertebral column with synthetic simulated soft tissue structures such as simulated discs positioned between vertebra and a simulated spinal cord and nerves. The skeletal structure produces a fluoroscopic image representative of human bone corresponding to the skeletal structure. A light source such as a plurality of LEDS is embedded in the visibly clear thermoplastic elastomer matrix adjacent to at least a portion of the skeletal structure, increasing the visibility of needle tracks formed in the visibly clear thermoplastic elastomer matrix. At least one heat source embedded in the visibly clear, thermoplastic elastomer matrix adjacent the vertebral column provides localized heating of a portion of the visibly clear thermoplastic elastomer matrix to fuse needle tracks formed in the matrix. In different embodiments, the model includes surgical hardware installed on the embedded vertebral column. Radiopaque markers may be embedded in the visibly clear thermoplastic elastomer matrix adjacent selected portions of the skeletal structure. The visibly clear thermoplastic matrix may include from about 15 wt % to about 20 wt % of a rubbery block copolymer such as an SEBS (styrene-ethylene/butylene-styrene) block copolymer and from about 80 wt % to about 85 wt % of a white oil. In one embodiment, the rubbery block copolymer has a tensile stress of from about 8.00 to about 10 psi, a tensile strength at break of from about 140 to about 170 psi and a tensile elongation at break of from about 500 to about 1500%.

Figure 8:
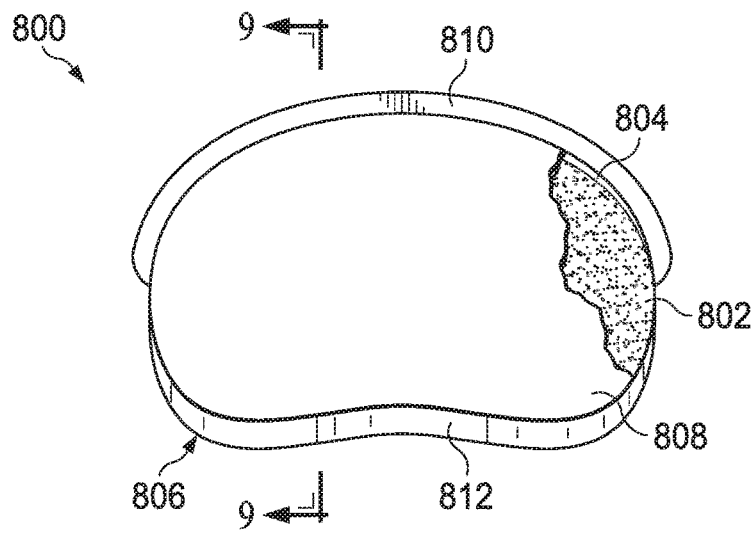
FIG. 8 is a partial perspective view of a first embodiment of a simulated intervertebral disc.

FIG. 8 is a partial perspective view of one embodiment of a simulated intervertebral disc 800, which may be used as disc 132 (FIG. 1) or 352 (FIG. 3A). As shown, simulated intervertebral disc 800 formed from a urethane foam core 802 impregnated with a thermoplastic elastomer gel which may be the same material as synthetic gel matrix 120 (FIG. 1). Foam core 802 simulates the nucleus pulposus of the intervertebral disc. The upper and lower surfaces 804, 806 of foam core 802 are covered with a thin layer 808 of silicone. Layer 808 may have a thickness of from about 0.5 to about 2.0 mm.

Figure 9:
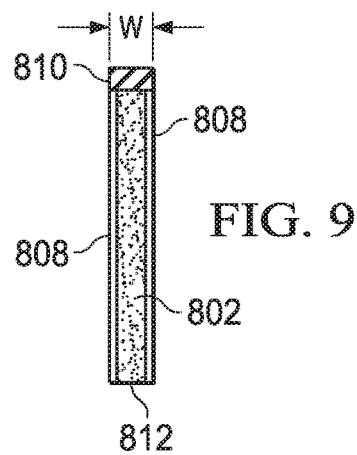
FIG. 9 is a cross sectional view of the simulated intervertebral disc of FIG. 8.

FIG. 9 is a cross section of the simulated disc 800 of FIG. 8. A thicker layer 810 of silicone extends around the periphery of disc 800. Depending upon the particular location of the disc in the vertebral column, layer 810 may extend around a portion or the entire periphery 812 of the foam core 802 and the width w of the layer may be varied depending upon the position of the disc in the vertebral column. Layer 810 simulates the annulus fibrosus of an intervertebral disc. The width w of layer 810 may be selectively varied around periphery 812 of the foam core 802 to maintain the desired spacing between the vertebrae. For example, discs 800 prepared for the lumbar portion of the vertebrae column may have additional silicone added to the anterior side of the periphery of the disc to more accurately simulate the spacing between the anterior portions of lumbar vertebrae in the lumbar portion of the vertebral column. In one embodiment, layer 810 may have a width and thickness of from about 3 to about 10 mm thick. Layer 810 and foam core 802 serve to simulate the "feel" of an actual intervertebral disc upon needle penetration, with layer 810 providing greater resistance to needle penetration than foam core 802 as a needle penetrates the simulated disc.

Figure 10:
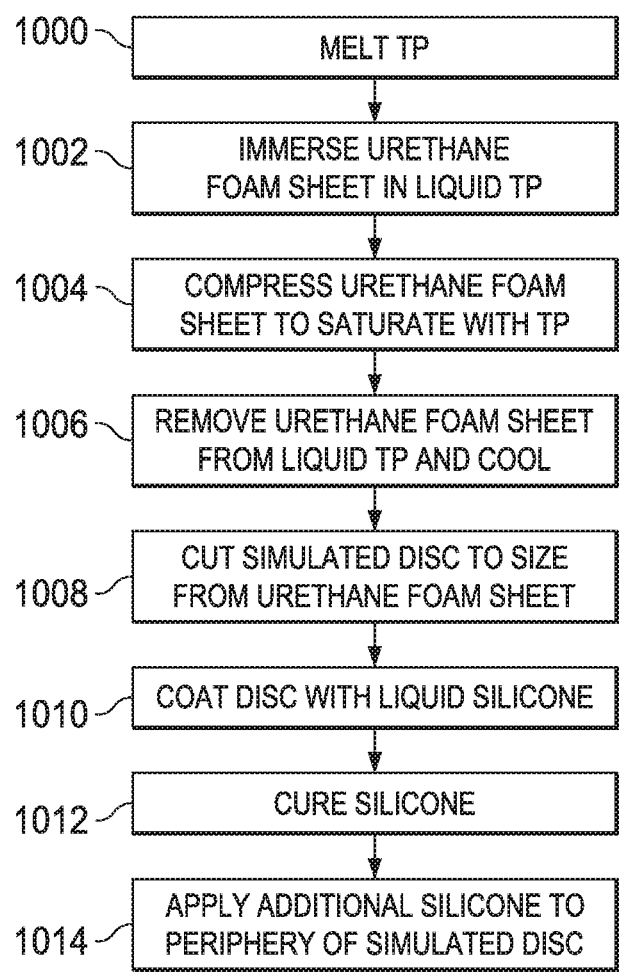
FIG. 10 is a flowchart for the preparation of the simulated intervertebral disc of FIG. 8.

In one embodiment, simulated discs, such as discs 352 (FIG. 3A) are formed from a sheet of open cell urethane foam having a nominal thickness of from ¼ to ½ inches. FIG. 10 is a flowchart illustrating preparation of the simulated discs. At step 1000, thermoplastic elastomer (TP) is placed in a suitable container and melted. The thermoplastic elastomer may be the same as used to form matrix 120 (FIG. 1), matrix 320 or a similar material. After the thermoplastic elastomer is liquefied, a sheet of open cell polyurethane foam is placed in the container and immersed in the liquid elastomer to fill the open cell foam with the thermoplastic elastomer at 1002. The open cell polyurethane sheet may be compressed at 1004 while immersed in the liquid elastomer to force air from the voids in the open cell foam and allow the liquid elastomer to saturate the foam.

At step 1006 the sheet is removed from the container and cooled to allow the thermoplastic elastomer to solidify. After curing, the thermoplastic elastomer impregnated open cell polyurethane foam sheet will have a thickness in the range of from about 3 mm to about 10 mm. A disc 800 (FIG. 8) is cut from the sheet at 1008. The disc is cut to a size and profile corresponding to the particular vertebrae that the disc will be placed between. The upper and lower surfaces of the disc, (e.g., the surfaces that will face the vertebrae) are coated with a layer of liquid silicone adhesive at step 1010 to form layer and allowed to cure at 1012. At step 1014, additional silicone is selectively applied around the periphery of the disc to simulate the annulus fibrosus of an actual intervertebral disc. In one embodiment, a high temperature liquid silicone sealant is used to coat the elastomer impregnated disc and add additional silicone around the periphery of the disc.

After the liquid silicone has cured, simulated intervertebral disc 800 is mounted between vertebrae 138 (FIG. 1) with a jig or support to form a skeletal structure that is then positioned in a mold. Additional silicone may be added to the periphery of simulated intervertebral discs 800 as the discs are between positioned vertebrae to more accurately simulate a spinal column. Liquid, visibly clear, thermoplastic elastomer is then poured into the mold as described above to form the spinal injection training model.

Figure 11:
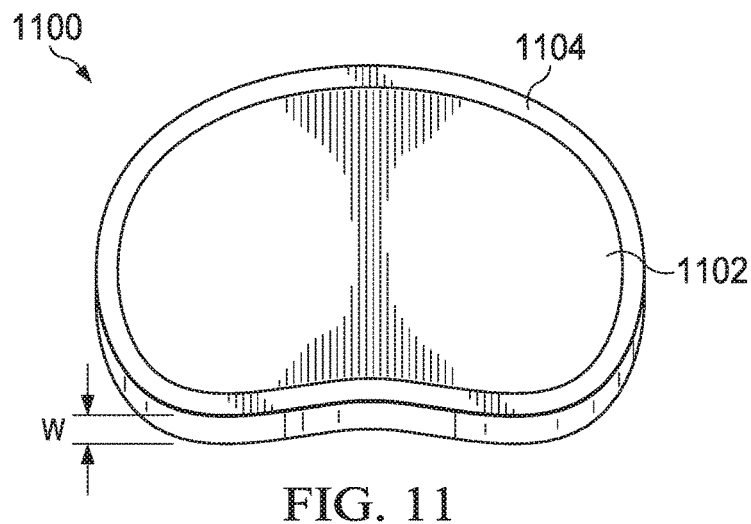
FIG. 11 is a partial perspective view of a second embodiment of a simulated intervertebral disc.

FIG. 11 is a partial perspective view of another embodiment of a simulated intervertebral disc. As illustrated, simulated intervertebral disc 1100 includes a core 1102 of thermoplastic elastomer. Thermoplastic elastomer core 1102 will typically have a thickness of from about 3 to about 10 mm. A band 1104 of a silicone or similar material extends around the periphery of core 1102. Band 1104 is selected to simulate the annulus fibrosus of an intervertebral disc while the thermoplastic elastomer of core 1102 while the thermoplastic elastomer of core 1102 is selected to simulate the nucleus pulposus of the intervertebral disc. Band 1104 and thermoplastic elastomer core 1102 serve to simulate the "feel" of an actual intervertebral disc upon needle penetration, with band 1104 providing greater resistant to needle penetration than thermoplastic elastomer core 1102.

To form simulated intervertebral disc 1100, may be formed by first molding thermoplastic elastomer core 1102. Liquid thermoplastic elastomer is poured into a mold of the desired dimensions and allowed to cure. Thermoplastic elastomer core 1102 will molded to a thickness in the range of from about 3 mm to about 10 mm depending upon its position in the vertebral column. Liquid silicone may then be applied around the circumference of thermoplastic elastomer core 1102 to the desired thickness and width. In one variation, a liquid high temperature silicone sealant may be used to form band 1102. Typically band 1104 will have a width and thickness of in the range of about 3 to about 10 mm. The width w of band 1104 may be selectively varied, depending upon its position in the vertebral column and around circumference of thermoplastic elastomer core 1102 to maintain the desired spacing between the vertebrae.

Alternatively, band 1104 may be molded or formed first. In one variation, band 1104 may be molded from a liquid high temperature silicone. After the band has been molded and cured, liquid thermoplastic elastomer is poured into the band to form core 1102. In this variation, band 1104 serves as a mold for thermoplastic elastomer core 1102.

Figure 12A:
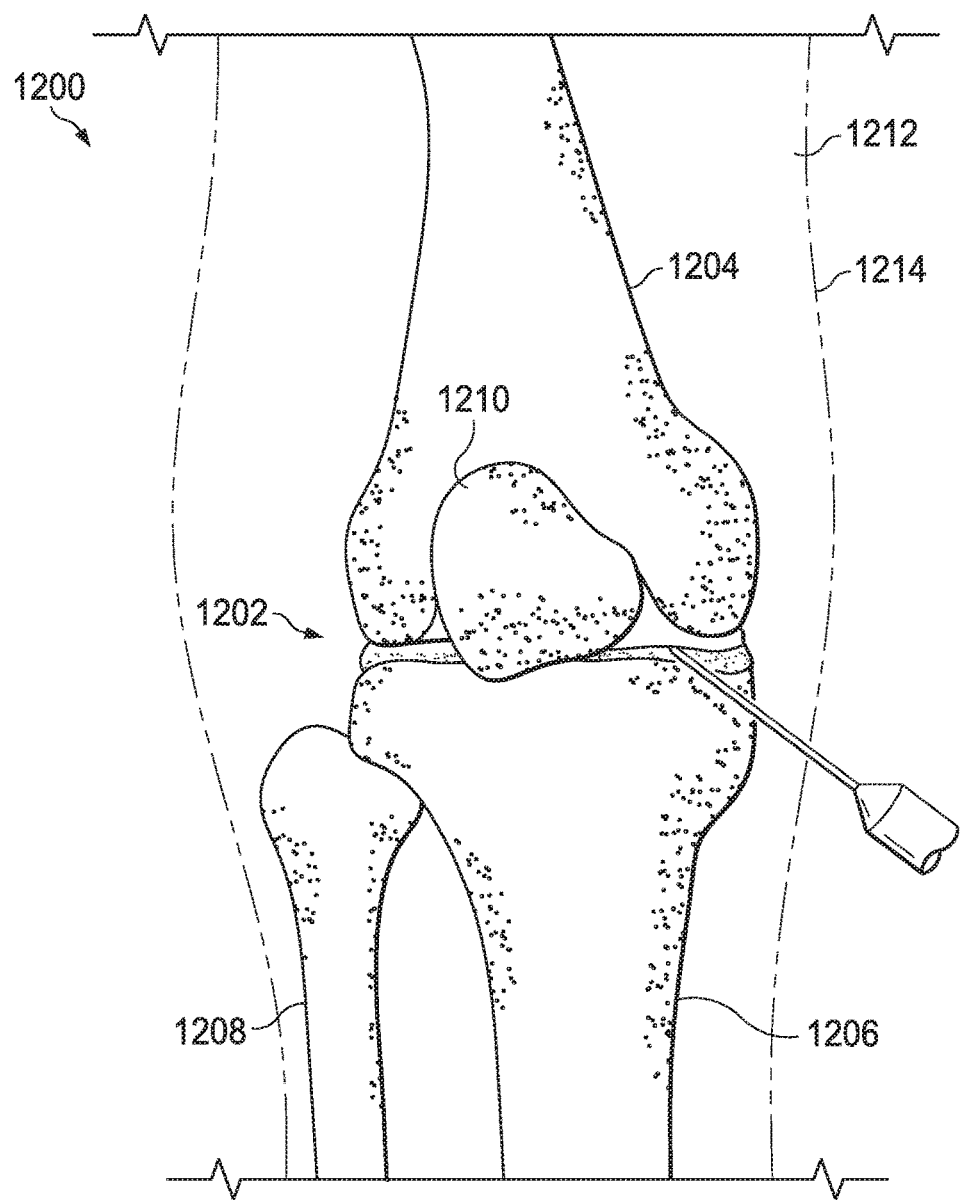
FIG. 12A is front partial perspective view illustrating a training model incorporating a knee joint.

FIG. 12A is front partial perspective view illustrating a training model 1200 incorporating a knee joint 1202. As illustrated, the model includes at least a portion of the major bones of the knees joint including a femur 1204, tibia 1206 and fibula 1208. Optionally, model 1200 may include a patella 1210. The femur 1204, tibia 1206, fibula 1208 and patella 1210 are embedded in a visibly clear, thermoplastic elastomer matrix 1212 similar or identical to synthetic gel 120. Visibly clear, thermoplastic elastomer matrix has a density and feel substantially similar that of human tissue to provide realistic haptic feedback upon needle insertion and placement. All or at least a portion of the surface 1214 of model 1200 is anatomically contoured to simulate a portion of a human leg including the knee to further enhance the model as a training tool. The bones are positioned within the visibly clear, thermoplastic elastomer matrix 1212 such that the bones are at the same position, relative to the anatomically contoured surface 1214 of model 1200, as the corresponding bones would be positioned within an actual human leg.

In an embodiment where the femur 1204, tibia 1206, fibula 1208 and patella 1210 are natural bone, the contrast produced during a fluoroscopically-guided procedure will realistically simulate that of an actual in vivo procedure. In other embodiments a suitable synthetic material that provides contrast representative of natural bone may be employed to form the bones.

Figure 12B:
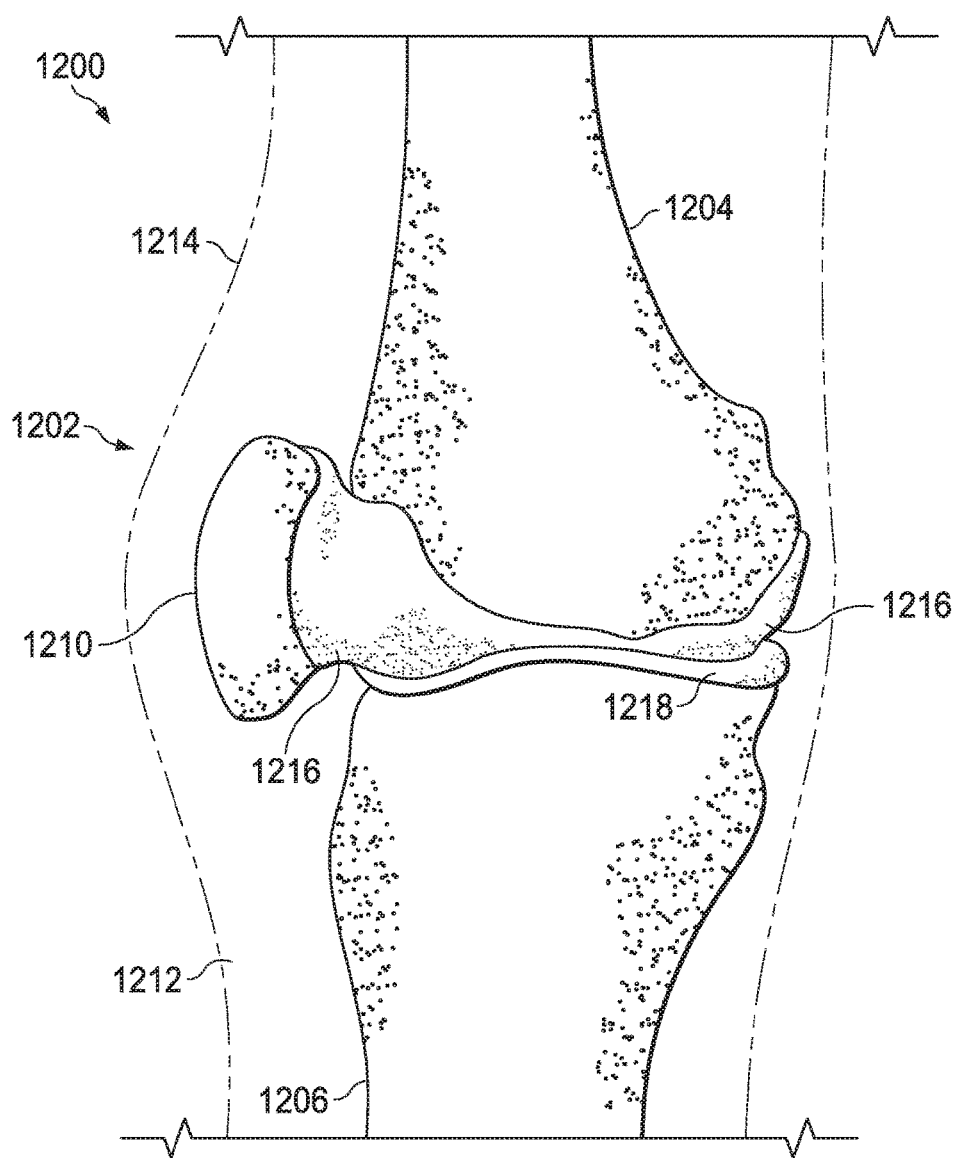
FIG. 12B is a side partial perspective view of the model of FIG. 12A.

FIG. 12B is a side partial perspective view of model 1200. Model 1200 is formed by placing femur 1204, tibia 1206, fibula 1208 and optionally patella 1210 in a mold having the contour of at least a portion of a human leg including the knee and embedding the bones in the visibly clear, thermoplastic elastomer matrix 1212. The bones may be glued to together or otherwise attached together prior to placing the bones into the mold. For example patella 1201 may be attached to femur 1204 and or tibia 1206 with a silicon adhesive or similar material 1216.

Soft tissue structures such as meniscus 1218 may be simulated with a synthetic material such as a silicon or silicon foam and positioned with or attached to the bones prior to or as the bones are placed in the mold. The simulated soft tissue structures may be selected to provide a different resistance to needle penetration than thermoplastic elastomer matrix 1212 such that one practicing injection with model. 1200 would know, by feel, when the needle penetrates the simulated soft tissue structure. The assembled joint 1202 or the bones comprising joint 1202 may be supported or braced in the mold with wires, ties or a jig prior to introducing the liquid thermoplastic elastomer matrix into the mold. After the liquid thermoplastic matrix 1212 has cooled, model 1200 may be removed from the mold.

Model 1200 may be used to practice injection techniques involving the knee. For example, as best illustrated in FIG. 12B, model 1200 may be used to simulate an injection of a steroid, such as cortisone, into the knee joint 1202 between femur 1204 and tibia 1206. It is anticipated that model 1200 may be used in training for other procedures involving the knee.

Figure 13:
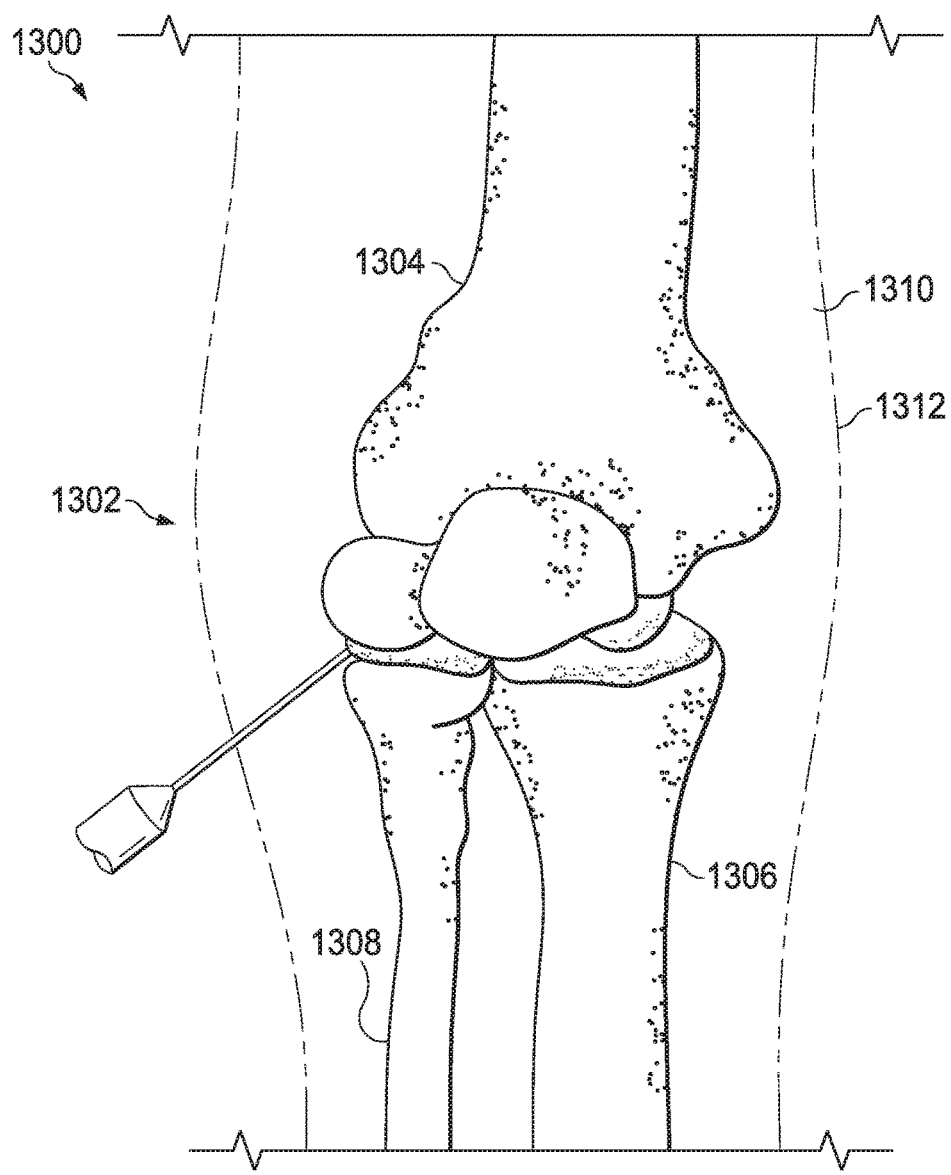
FIG. 13 is a is partial perspective view of a training model incorporating an elbow joint.

FIG. 13 is partial perspective view of a training model 1300 incorporating an elbow joint 1302. As illustrated, model 1300 includes a least a portion of a real or simulated humerus 1304, ulna 1306 and radius 1308. Similar to model 1200, the bones (humerus 1304, ulna 1306 and radius 1308) or at least some, or a portion of some of the bones, of elbow joint 1302 may natural bone or a a suitable synthetic material that provides contrast representative of natural bone during a fluoroscopically-guided procedure. Model 1302 is formed with a contoured surface 1312 that matches or simulates the contours of at least a portion of a human arm incorporating the elbow.

Model 1300 is formed in the same manner as model 1200. The bone comprising joint 1302 may be glued or otherwise attached together, positioned in a mold and imbedded in a liquid visibly clear, thermoplastic elastomer matrix 1310 similar or identical to synthetic gel 120. The bones comprising joint 1302 are positioned within the visibly clear, thermoplastic elastomer matrix 1310 such that the bones are at the same position, relative to the anatomically contoured surface 1312 of model 1300, as the corresponding bones would be positioned within an actual human arm.

Soft tissue structures of the elbow joint may be simulated with an appropriate material such as silicon or a synthetic foam such as a urethane or silicon foam and positioned on or attached to the bones before the liquid elastomer is poured into the mold. After the thermoplastic elastomer has cooled, model 1300 may be removed from the mold and used to simulate procedures involving injections into a human elbow. For example, as shown, model 1300 may be used to simulate an injection of, for example, a steroid such as cortisone into the elbow joint 1302.

Figure 14:
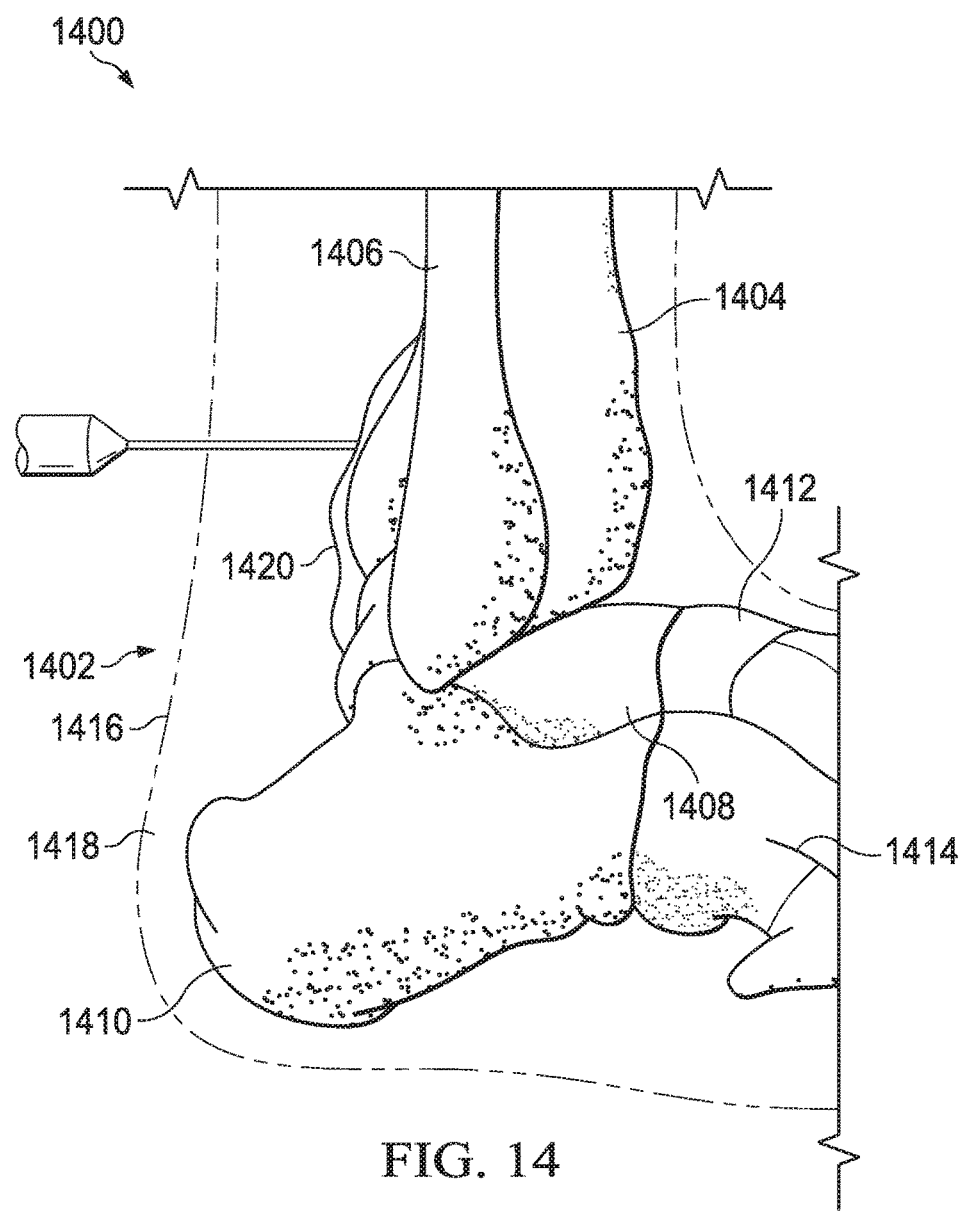
FIG. 14 is a side partial perspective view of a training model including an ankle joint.

FIG. 14 is a side partial perspective view of a training model 1400 including an ankle joint 1402. As illustrated, model 1400 includes at least part of the major bones of ankle including distal portions of the tibia 1404 and fibia 1406, the talus 1408 and the calcaneus 1410. The model may also include all or portions of the navicular 1412 and cuboid 1414 bones. In different embodiments, model 1400 may incorporate all of the bones of the ankle and foot. At least a portion of the surface 1416 of model 1400 is molded to the same anatomical contours as an actual human ankle for training purposes. The bones (tibia 1404, fibia 1406, talus 1408 calcaneus 1410, navicular 1412 and cuboid 1414 bones), or at least some, or a portion of some of the bones of ankle joint 1402, may natural bone or a suitable synthetic material that provides contrast representative of natural bone during a fluoroscopically-guided procedure.

Model 1400 is formed in the same manner as described in connection with model 1200, with the bones of ankle joint 1402 embedded in a thermoplastic elastomer matrix 1418 at the same positions, relative to the anatomically contoured surface 1416 of the model, as the corresponding bones of an actual human ankle would be positioned within a human. Visibly clear, thermoplastic elastomer matrix 1418 may be the same as, or similar to, synthetic gel matrix 120.

Soft tissue structures such as cartilage, tendons, ligaments and nerves may be simulated in model 1400 with suitable synthetic materials. For example nerves may be simulated with a colored wire, line or cord for training purposes. For example, as illustrated in FIG. 14, tibial nerve 1420 may be represented by a wire, cord or line, visible within matrix 1418 such that model 1400 may be used to simulate an injection to block the tibial nerve.

Figure 15A:
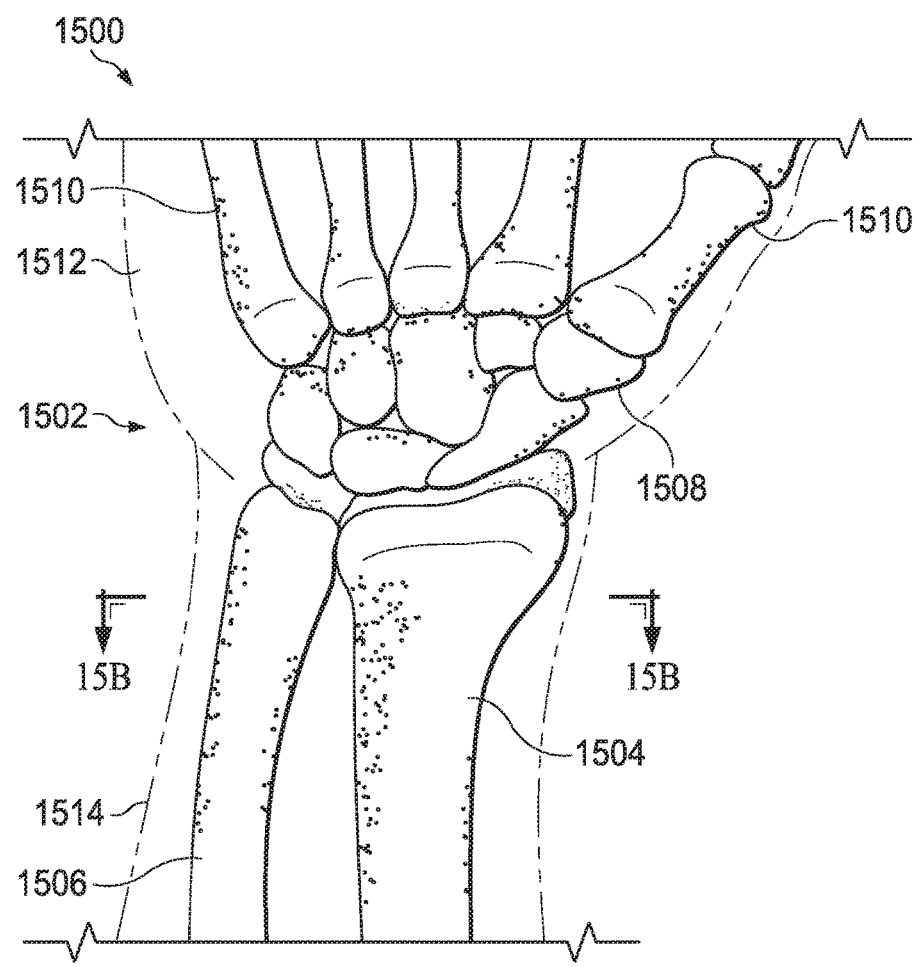
FIG. 15A is a partial perspective view of a training model including a human wrist joint.

FIG. 15A is a partial perspective view of a training model 1500 of a human wrist joint 1502. As illustrated, model 1500 includes the major bones of a wrist joint, including the radius 1504, ulna 1506 and carpels 1508. Model 1500 may also include some or all of the metacarpals 1510. In other embodiments, model 1500 may include all of the bones of the wrist and hand. Model 1500 may also include some or all of the metacarpals 1510. Model 1500 is formed in the same or similar manner as model 1200 with the bones (radius 1504 ulna 1506, carpels 1508 and metacarpals 1510 embedded in a visibly clear thermoplastic elastomer 1512 the same or similar to synthetic gel matrix 120. Model 1500 is molded with at least a portion of the surface 1514 of the model having the same anatomical contour or contours as the corresponding portions of an actual human wrist with the bones of the model positioned accordingly. Similar to model 1200, the bones of model 1500 are natural bone, human bone or formed from a synthetic material that produces an image contrast representative of natural bone during a fluoroscopically-guided procedure.

Figure 15B:
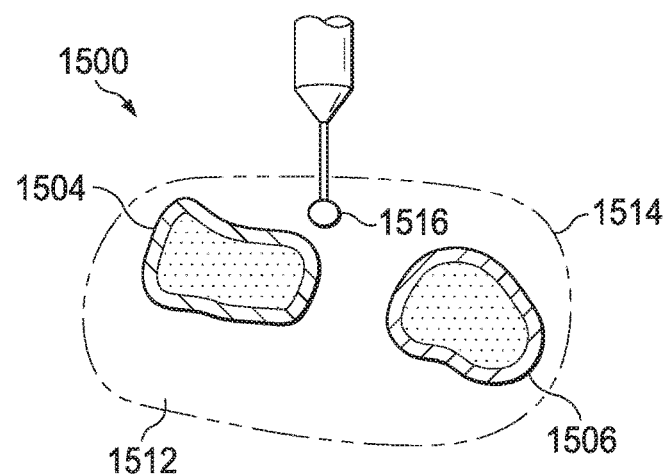
FIG. 15B a cross-section view of the model of FIG. 15A.

FIG. 15B is a cross-section view of the model of FIG. 15A taken along line A-A' of FIG. 15A. Model 1500 may include soft tissue structures such as cartilage, tendons, ligaments and nerves. Such soft tissue structures may be formed from suitable synthetic materials such as urethane, silicon, nylon or similar materials. As illustrated, the median nerve 1516 is represented in model 1500 as a synthetic cord, line, or similar material. FIG. 15A illustrates model 1500 being used to simulate an injection of a nerve block to median nerve 1516. It will be appreciated that model 1500 may be used to simulate a variety of injections into wrist joint 1502.

Figure 16:
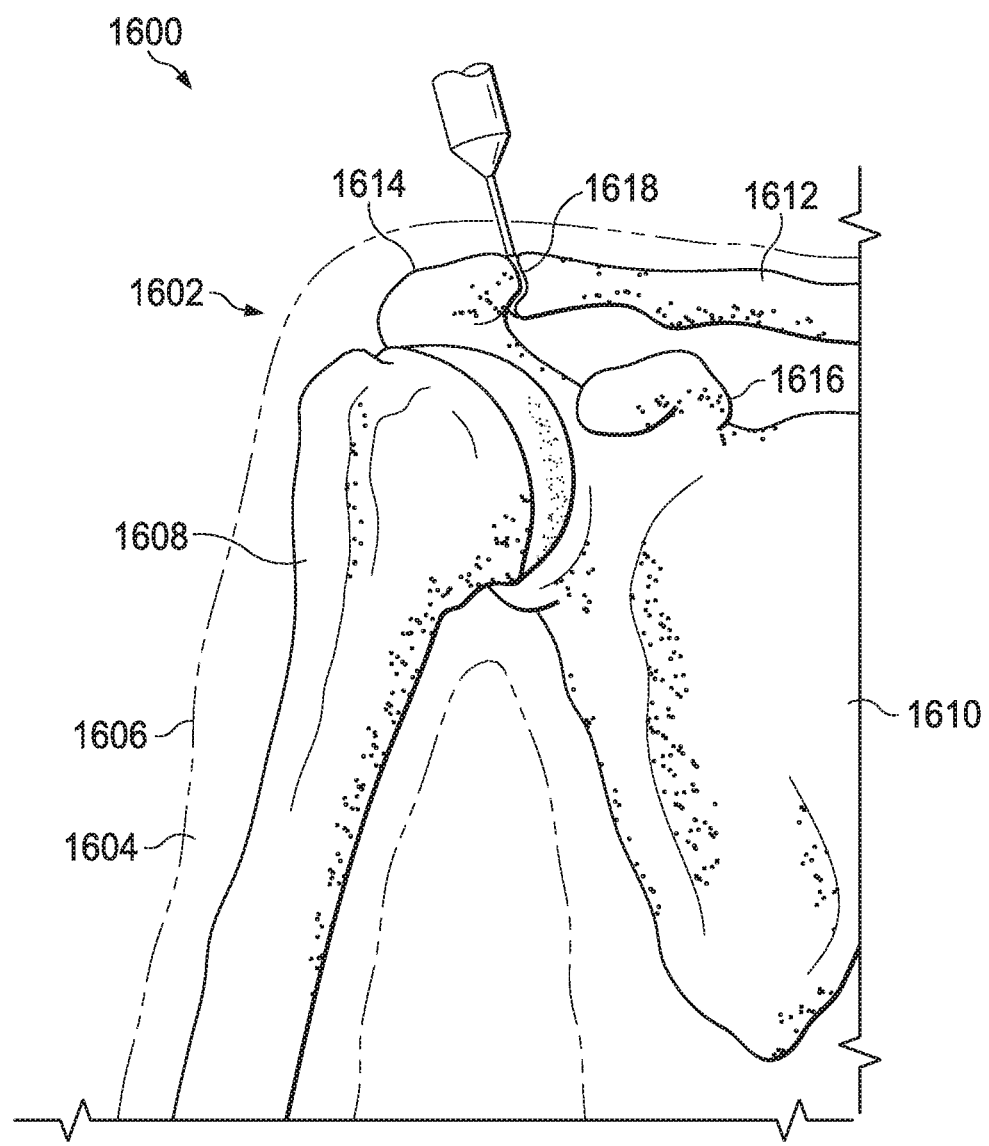
FIG. 16 is a partial perspective view of a training model including bones of a human shoulder embedded in a visibly clear thermoplastic elastomer.

FIG. 16 is a partial perspective view of a training model 1600 including the bones of a human shoulder 1602 embedded in a visibly clear thermoplastic elastomer 1604 at the same positions as the corresponding bones of an actual human shoulder relative to the contoured surface 1606 of model 1600. As illustrated, model 1600 includes the major bones of a human shoulder joint including at least the head of the humerus 1608, at least a portion of the scapula 1610, the clavicle 1612, the acromion 1614 and the coracoid process 1616. Bones 1608-1616 may natural bone or a suitable synthetic material that provides contrast representative of natural bone during a fluoroscopically-guided procedure. Model 1600 may include simulated soft tissue structures including cartilage, tendons, ligaments, nerves. Such structures may be made from suitable synthetic materials that provide differing degrees of resistance to needle penetration to aid in injection training.

Model 1600 may be used to simulate a variety of injections into a human shoulder. For example, as illustrated, model 1600 may be used to simulate an injection into the acromioclavicular joint 1618 for the treatment of pain. As will be appreciated, model 1600 may be utilized in simulating a wide variety of injections into the shoulder.

Figure 17:
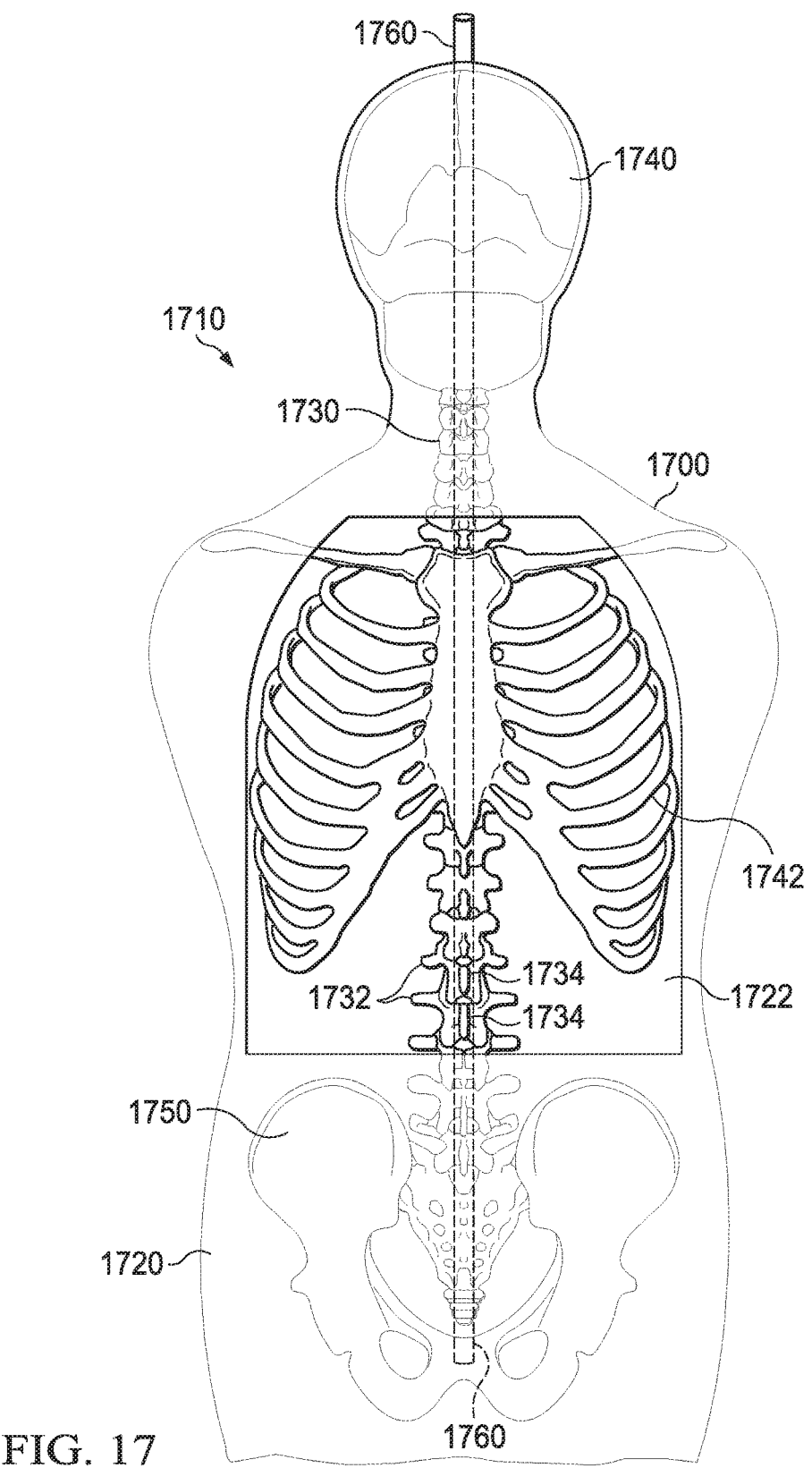
FIG. 17 is a partial perspective view of a training model including a skeletal structure with at least a portion of a vertebral column with a synthetic spinal sheath passing though the vertebral column.

FIG. 17 is a top view of another embodiment of a spinal injection training model 1700. As shown, model 1700 includes a partial skeletal structure 1710 including complete vertebral column 1730 with vertebra 1732, simulated intervertebral discs 1734, skull 1740 and pelvic bone 1750 embedded in synthetic gel matrix 1720. Simulated intervertebral discs 1740 may be the same as or similar to synthetic intervertebral discs 800 and 1100 (FIGS. 8-11) described above.

Model 1700 further includes ribs 1742 and a simulated synthetic spinal sheath (meninges) 1760 passing through at least a portion of vertebral column 1730. In different variations, less than a complete vertebral column may be included in skeletal structure 1710 and portions of skeletal structure 1710, such as skull 1740 and ribs 1742 may be omitted and/or different skeletal components may be added. Matrix 1720 is a transparent synthetic ballistic gel having a density and feel substantially similar that of human tissue as described above in connection with FIGS. 1 and 2. In one embodiment, a void or cavity 1722 is formed in the area corresponding to the thoracic and abdominal cavities during the molding process as described in further detail below.

Simulated synthetic spinal sheath 1760 is formed from a material selected to provide tactile feedback when penetrated with a needle similar to the "pop" or sudden release that a practitioner feels when inserting a needle through the myelin sheath surrounding the spinal cord. The material from which synthetic spinal sheath 1760 is formed is flexible and elastic and exhibits a degree of resistance to needle penetration sufficient to simulate needle penetration of a natural human myelin spinal sheath. In one embodiment, synthetic spinal sheath 1760 is formed from a flexible latex rubber surgical tubing having an exterior diameter of ⅝ inch, and internal diameter of ⅜ inch and wall thickness of ⅛ inch available from GF Health Products, Inc. As illustrated, the tubing forming synthetic spinal sheath 1760 is passed through an opening in skull 1740, vertebra 1732, simulated intervertebral discs 1734 and pelvic bone 1750.

Referring to FIG. 18a-c synthetic spinal sheath 1760 provides a means of training practitioners in spinal injections by simulating the feel of a needle penetrating the spinal sheath (meninges). In practice, a needle 1762 contacts and initially distends synthetic spinal sheath 1760 as illustrated in FIG. 18a. The pressure of the needle against the synthetic spinal sheath is increased until the needle penetrates the sheath as illustrated in FIG. 18b. When the needle penetrates the sheath, the force resisting the needle penetration is suddenly removed, resulting in a tactile "pop" or release that is readily discernable by the practitioner. The needle then penetrates further with reduced applied force. In one embodiment, a latex rubber tubing is utilized as synthetic spinal sheath 1760; however, in different embodiments, other materials providing the same or similar needle penetration characteristics may be used.

Figure 19:
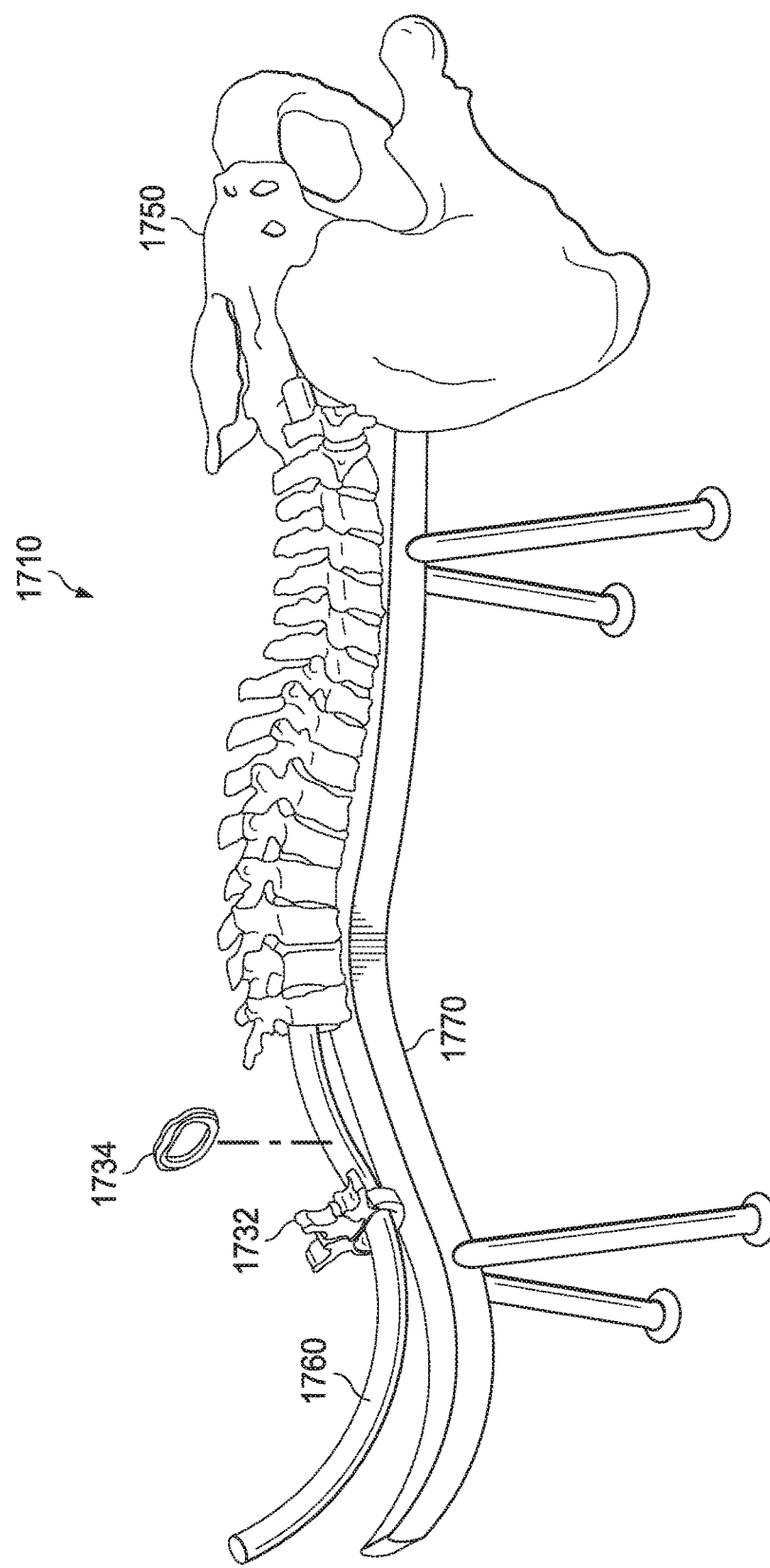
FIG. 19 is a partial perspective view illustrating assembly of the skeletal structure of the model of FIG. 17.

FIG. 19 is a partial perspective view illustrating assembly of skeletal structure 1710. A jig 1770 having a curvature approximating a natural human spinal column is employed to hold pelvic bone 1750, vertebra 1732 and simulated intervertebral discs 1734 as the vertebra and discs are placed over the tubing forming synthetic spinal sheath 1760. As vertebra 1732 and simulated intervertebral discs 1734 are positioned on simulated spinal sheath 1760, additional silicone may be placed between the vertebra to aid in spacing and positioning the vertebra and simulated intervertebral discs. Pelvic bone 1750 may be glued to the adjacent vertebra 1732 to retain it in position during assembly.

Figure 20:
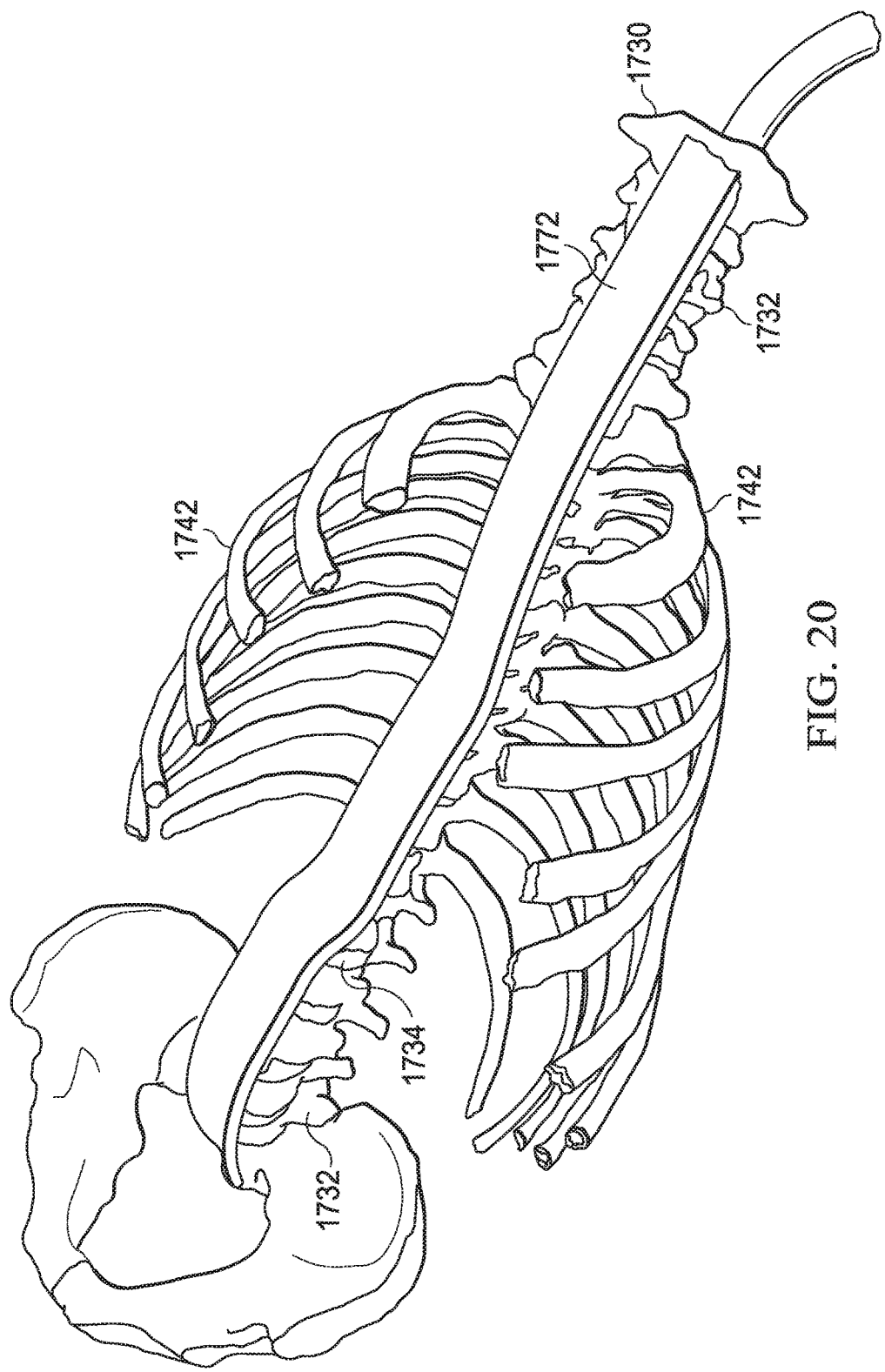
FIG. 20 is a perspective view of the skeletal structure of the model of FIG. 17.

FIG. 20 is a partial perspective view of skeletal structure 1710. After vertebra 1732 and simulated intervertebral discs 1734 have been positioned on synthetic spinal sheath 1760, a rigid curved retaining strip 1772 is glued to the vertebra to hold vertebral column 1730 in position. Retainer strip 1772 is selected from a radio transparent material so that the strip does not interfere with x-ray or fluoroscopic images of skeletal structure 1710 when model 1700 is in use. In one variation, retainer strip 1772 is formed from a fiber glass cloth impregnated with a thermosetting resin. Strip 1772 is cut from the resin impregnated fiber glass cloth, placed on a jig having a curvature similar to a natural spinal column and heated to set the resin. After vertebral column 1730 is secured on retaining strip 1772, ribs 1742 are glued to vertebra 1732. Synthetic spinal sheath 1760 is then placed through skull 1740 and the skull secured to the vertebral column 1730.

Figure 21:
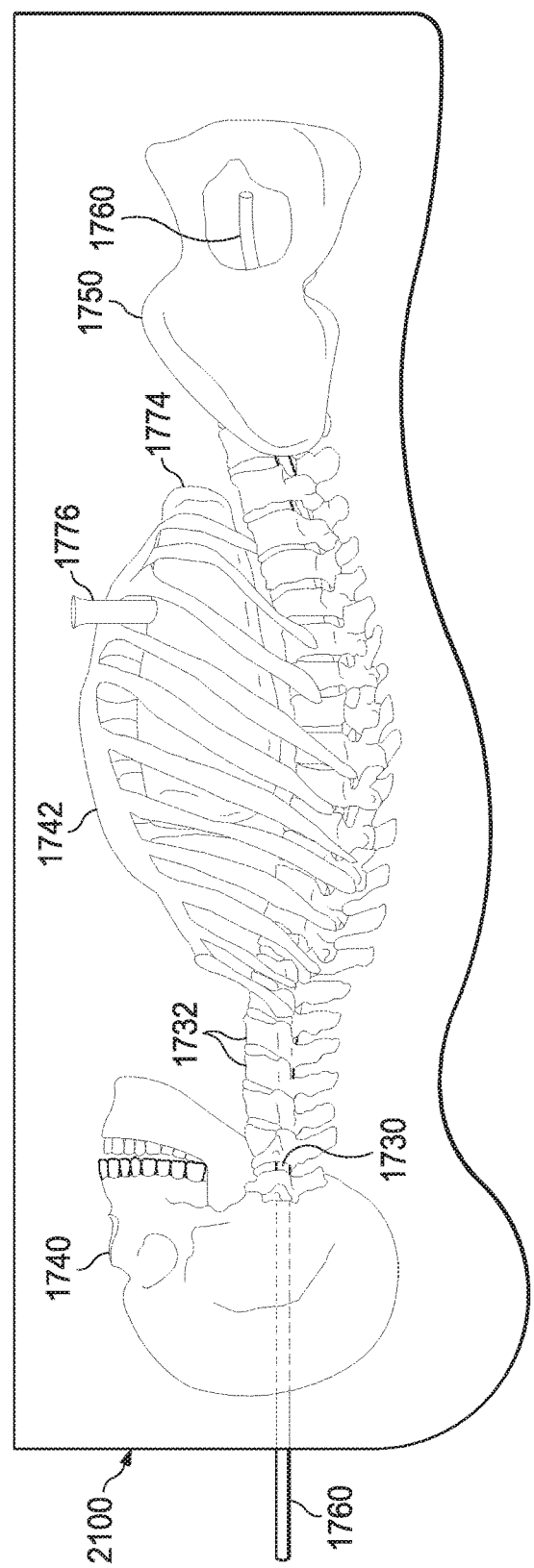
FIG. 21 is a perspective view of the skeletal structure of FIG. 20 positioned in a mold.

FIG. 21 is a side view of completed skeletal structure 1710 positioned in a mold 2100. As illustrated, mold 2100 has a bottom surface with contours approximating a human back. Skeletal structure 1700 may be supported and positioned in mold 2100 with wires or similar heat resistant fasteners. Heat resistant thread or sting such as a Teflon filament may be used to space and hold ribs 1742 in position. Skull 1740 may be glued to the adjacent vertebra and is retained in position by synthetic spinal sheath 1760 which passes through the wall of mold 2100.

After skeletal structure 1710 is positioned in mold 2100, liquid thermoplastic gel is poured into the mold around the skeletal structure to form model 1700. During the molding process, spinal sheath 1760 extends through a hole in mold 2100 with a first end 1764 of synthetic spinal sheath positioned outside of mold 2000 and left open so that expanding gas in the sheath may escape without distending the sheath. The second end (not shown) of synthetic spinal sheath 1760 is sealed with a high temperature silicone and positioned adjacent pelvic bone 1750 during the molding process.

A heat resistant bladder 1774 may be inserted into the space corresponding to the thoracic and/or abdominal cavity of model 1700 and inflated through port 1776 prior to molding the thermoplastic gel around skeletal structure 1710 to form cavity 1722 (FIG. 17). Heat resistant bladder 1774 may be formed from a silicone sheet or film and coated with a release agent prior to molding model 1700. After the thermoplastic gel has cooled and solidified, the release agent allows bladder 1774 to be removed from the synthetic gel matrix 1720 (FIG. 17) of model 1700 though a relatively small opening, such as the opening formed by port 1776. Bladder 1774 can displace a significant portion of the thermoplastic gel to form cavity 1722 thereby reducing the weight of model 1700. In one variation, bladder 1774 may displace 10, 20, 30 or 40 percent of the volume of thermoplastic gel that would otherwise be used to form model 1700. The use of bladder 1774 to form cavity 1722 (FIG. 17) reduces the weight of model 1700 from 10 to 40 percent, allowing the model to be transported and positioned with significantly less effort.

It will be appreciated by those skilled in the art having the benefit of this disclosure that the spinal injection trainer and method described herein may be configured for multiple adaptations based on selected criteria. For example, as will be appreciated, in different embodiments, training models 1200, 1300, 1400, 1500 and 1600 may include more or less structure than illustrated and described. For example, in some models, a greater or lesser number of actual or simulated bones and soft tissue structures may be incorporated into the models. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A model for anatomic training and injection practice, comprising:
   a visibly transparent, thermally fusible synthetic gel matrix formed with at least one contoured surface, the contoured surface simulating a partial human torso;
   a skeletal structure including at least a portion of a vertebral column embedded within the synthetic gel matrix at the same location as the corresponding skeletal structure is located in a human, at least a portion of the skeletal structure being radiopaque for producing a fluoroscopic image with an image contrast representative of human bone;
   a synthetic spinal sheath passing through at least a portion of the vertebral column, the synthetic spinal sheath providing tactile feedback upon needle penetration that simulates the tactile feedback of a needle penetrating a natural human spinal sheath; and
   the synthetic gel matrix retaining visible tracks resulting from needle penetration and extraction of a needle along the path of the needle after insertion at a point on the contoured surface to a target below the contoured surface, at least a portion of the needle tracks extending along the path remaining visible until the needle tracks are fused closed with a heat source such that the needle tracks are no longer visible in the synthetic gel matrix.

2. The model of claim 1 wherein the synthetic spinal sheath is formed from elastic flexible tubing with a resistance to needle penetration sufficient to simulate needle penetration of a human myelin spinal sheath.

3. The model of claim 1 wherein the synthetic spinal sheath is formed from flexible elastic latex tubing.

4. The model of claim 3 wherein the flexible elastic latex tubing has a wall thickness of ⅜ inch.

5. The model of claim 3 wherein the flexible elastic latex tubing has an inside diameter of ⅜ inch, an outside diameter of ⅝ inch and a wall thickness of ⅜ inch.

6. The model of claim 1 further comprising at least one synthetic simulated soft tissue structure embedded in the synthetic gel matrix, the synthetic simulated soft tissue structure embedded in the synthetic gel matrix at a position corresponding to the same location, relative to the contoured surface, as the corresponding soft tissue structure is located in a human torso.

7. The model of claim 6 wherein the synthetic simulated soft tissue structure comprises at least one synthetic intervertebral disc that simulates the density of a human vertebral disc.

8. The model of claim 1 further comprising surgical hardware installed on the embedded skeletal structure.

9. The model of claim 1 further comprising at least one heat source embedded in the synthetic gel matrix adjacent the embedded skeletal structure.

10. The model of claim 1 further wherein the at least a portion of the skeletal structure producing a fluoroscopic image with an image contrast representative of human bone is comprised of human bone from a cadaver.

11. A method of making a model for anatomic training and injection practice, comprising:
assembling a skeletal structure with at least a portion of a vertebral column including a synthetic spinal sheath passing through the at least a portion of the vertebral column, the synthetic spinal sheath providing tactile feedback upon needle penetration that simulates the tactile feedback of a needle penetrating a natural human spinal sheath, at least a portion of the vertebral column being radiopaque for producing a fluoroscopic image representative of the structure of human bone;
positioning the skeletal structure in a mold having a contoured portion simulating a partial torso; and
embedding the skeletal structure in a visibly transparent, thermally fusible, synthetic ballistic gel matrix, wherein, upon curing, the skeletal structure is positioned, relative to the contoured surface, at the same location as the corresponding skeletal structure is located in a human torso, and wherein at least a portion of visible needle tracks formed through the synthetic gel matrix along the path of a needle upon insertion at a point on the contoured surface to a target below the contoured surface remain visible until the needle tracks are fused closed with a heat source such that the needle tracks are no longer visible in the synthetic gel matrix.

12. The method of claim 11 wherein the synthetic spinal sheath is formed from elastic flexible tubing with a resistance to needle penetration sufficient to simulate needle penetration of a human myelin spinal sheath.

13. The method of claim 11 wherein the synthetic spinal sheath is formed from flexible elastic latex tubing.

14. The method of claim 13 wherein the flexible elastic latex tubing has a wall thickness of 3/8 inch.

15. The method of claim 13 wherein the flexible elastic latex tubing has an inside diameter of 3/8 inch, an outside diameter of 5/8 inch and a wall thickness of 3/8 inch.

16. The method of claim 11 further comprising positioning at least one synthetic intervertebral disc in the vertebral column within the form.

17. The method of claim 11 further comprising positioning a flexible bladder within the skeletal structure at a location corresponding to the thoracic cavity before embedding the skeletal structure in a visibly clear, thermally fusible, synthetic ballistic gel matrix.

18. The method of claim 17 further comprising removing the bladder after the visibly clear, thermally fusible, synthetic ballistic gel matrix has solidified.

* * * * *